(12) United States Patent
Johnson

(10) Patent No.: US 9,884,027 B2
(45) Date of Patent: Feb. 6, 2018

(54) NANOFIBER SCAFFOLDS FOR BIOLOGICAL STRUCTURES

(71) Applicant: NANOFIBER SOLUTIONS, INC., Hilliard, OH (US)

(72) Inventor: Jed K. Johnson, London, OH (US)

(73) Assignee: NANOFIBER SOLUTIONS, INC., Hilliard, OH (US)

( * ) Notice: Subject to any disclaimer, the term of this patent is extended or adjusted under 35 U.S.C. 154(b) by 317 days.

(21) Appl. No.: 13/740,913

(22) Filed: Jan. 14, 2013

(65) Prior Publication Data

US 2014/0030315 A1  Jan. 30, 2014

Related U.S. Application Data

(60) Provisional application No. 61/585,869, filed on Jan. 12, 2012.

(51) Int. Cl.
| | | |
|---|---|---|
| *A61K 35/12* | (2015.01) | |
| *A61K 9/70* | (2006.01) | |
| *A61K 47/32* | (2006.01) | |
| *A61L 27/38* | (2006.01) | |
| *A61L 27/54* | (2006.01) | |
| *A61L 27/60* | (2006.01) | |

(52) U.S. Cl.
CPC .............. *A61K 9/70* (2013.01); *A61K 35/12* (2013.01); *A61K 47/32* (2013.01); *A61L 27/3804* (2013.01); *A61L 27/54* (2013.01); *A61L 27/60* (2013.01); *A61L 2300/252* (2013.01); *A61L 2300/406* (2013.01); *A61L 2300/41* (2013.01); *A61L 2300/414* (2013.01)

(58) Field of Classification Search
None
See application file for complete search history.

(56) References Cited

U.S. PATENT DOCUMENTS

| | | | |
|---|---|---|---|
| 4,738,740 A | 4/1988 | Pinchuk et al. | |
| 5,628,788 A | 5/1997 | Pinchuk | |
| 6,143,022 A | 11/2000 | Shull et al. | |
| 7,115,220 B2 | 10/2006 | Dubson et al. | |
| 7,220,281 B2 | 5/2007 | Lambrecht et al. | |
| 7,390,760 B1 | 6/2008 | Chen et al. | |
| 7,490,563 B2 | 2/2009 | Eastin et al. | |
| 7,629,030 B2 | 12/2009 | Robertson et al. | |
| 8,157,722 B2 | 4/2012 | Arnal et al. | |
| 2002/0090725 A1 | 7/2002 | Simpson et al. | |
| 2003/0168756 A1 | 9/2003 | Balkus, Jr. et al. | |
| 2003/0226750 A1* | 12/2003 | Fenn ..................... | 204/164 |
| 2005/0277985 A1 | 12/2005 | Wert et al. | |
| 2006/0060999 A1 | 3/2006 | Amagasa et al. | |
| 2006/0085063 A1 | 4/2006 | Shastri et al. | |
| 2006/0134157 A1 | 6/2006 | Lehman et al. | |
| 2006/0135020 A1 | 6/2006 | Weinberg et al. | |
| 2006/0154063 A1 | 7/2006 | Fujihara et al. | |
| 2006/0204539 A1 | 9/2006 | Atala et al. | |
| 2007/0142907 A1 | 6/2007 | Moaddeb et al. | |
| 2007/0191956 A1 | 8/2007 | Prewett et al. | |
| 2007/0232169 A1 | 10/2007 | Strickler et al. | |
| 2007/0269481 A1 | 11/2007 | Li et al. | |
| 2008/0208358 A1 | 8/2008 | Bellamkonda et al. | |
| 2009/0018643 A1 | 1/2009 | Hashi et al. | |
| 2009/0108503 A1 | 4/2009 | Scott-Carnell et al. | |
| 2009/0152773 A1 | 6/2009 | Barinov et al. | |
| 2009/0162468 A1 | 6/2009 | Barinov et al. | |
| 2009/0253328 A1 | 10/2009 | Watanabe et al. | |
| 2010/0166854 A1 | 7/2010 | Michniak-Kohn et al. | |
| 2010/0222771 A1 | 9/2010 | Mitchell et al. | |
| 2010/0233115 A1 | 9/2010 | Patel et al. | |
| 2010/0273258 A1 | 10/2010 | Lannutti et al. | |
| 2010/0303881 A1 | 12/2010 | Hoke et al. | |
| 2011/0022149 A1 | 1/2011 | Cox et al. | |
| 2011/0028834 A1 | 2/2011 | Zussman | |
| 2011/0030885 A1 | 2/2011 | Anneaux et al. | |
| 2011/0083987 A1 | 4/2011 | Rolland et al. | |
| 2011/0098826 A1 | 4/2011 | Mauck et al. | |
| 2011/0166647 A1 | 7/2011 | Hashi et al. | |
| 2011/0177395 A1 | 7/2011 | Kamisasa | |
| 2012/0068384 A1 | 3/2012 | Phaneuf et al. | |
| 2012/0093717 A1 | 4/2012 | Mauck et al. | |
| 2013/0103079 A1 | 4/2013 | Lau et al. | |
| 2013/0310920 A1 | 11/2013 | Su | |
| 2014/0057346 A1 | 2/2014 | Johnson | |
| 2014/0072951 A1 | 3/2014 | Johnson | |
| 2014/0272225 A1 | 9/2014 | Johnson | |
| 2014/0309726 A1 | 10/2014 | Wang | |
| 2015/0105799 A1 | 4/2015 | Lohmeier et al. | |
| 2017/0182206 A1 | 6/2017 | Johnson et al. | |

FOREIGN PATENT DOCUMENTS

| | | |
|---|---|---|
| CN | 102008755 A | 4/2011 |
| EP | 0416846 A2 | 3/1991 |

(Continued)

OTHER PUBLICATIONS

Nam J, Johnson J, Lannutti JJ, Agarwal S. "Modulation of embryonic mesenchymal progenitor cell differentiation via control over pure mechanical modules in electrospun nanofibers." Apr. 2011;7(4):1516-24. doi: 10.1016/j.actbio.2010.11.022. Epub Nov. 22, 2010.

D Li, Y Wang, Y Xia "Electrospinning nanofibers as uniaxially aligned arrays and layer-by-layer stacked films", Advanced Materials, vol. 16, No. 4, Feb. 2004 (Feb. 2004) pp. 361-366.

Frey et al. "Electrospinning and Porosity Measurements of Nylon6 PEO blended Nonwovens" Journal of Engineered Fibers and Fabrics (2007), 2(1):31-37.

Hashi et al. "Antithrombogenic Modification of Small Diameter Microfibrous Vascular Grafts" Arterioscler Thromb Vasc Biol. (Aug. 2010), 30(8):1621-1627.

(Continued)

*Primary Examiner* — Robert M Kelly
(74) *Attorney, Agent, or Firm* — Pepper Hamilton LLP

(57) ABSTRACT

A system for manufacturing an artificial construct suitable for transplantation into a biological organism that includes a two or three-dimensional preform that is based on the actual two or three-dimensional structure of a native mammalian tissue; and an electrospinning apparatus, wherein the electrospinning apparatus is operative to deposit at least one layer of polymer fibers on the preform to form a polymer scaffold, and wherein the orientation of the fibers in the scaffold relative to one another is substantially parallel.

15 Claims, 13 Drawing Sheets

(56) References Cited

FOREIGN PATENT DOCUMENTS

| EP | 2422003 | 10/2010 |
|---|---|---|
| JP | 2012-527217 A | 11/2012 |
| WO | WO 2001/015754 A1 | 3/2001 |
| WO | WO 2005/012606 A2 | 2/2005 |
| WO | WO 2006/138552 A2 | 12/2006 |
| WO | WO 2008/137659 A1 | 11/2008 |
| WO | WO 2009/089035 A1 | 7/2009 |
| WO | 2010040129 A2 | 4/2010 |
| WO | WO 2010/048281 | 4/2010 |
| WO | WO 2010/124207 A1 | 10/2010 |
| WO | WO 2013/078051 A1 | 5/2013 |
| WO | WO 2013/106822 A1 | 7/2013 |
| WO | WO 2014/031721 A1 | 2/2014 |
| WO | WO 2014/145864 A1 | 9/2014 |
| WO | WO 2015/153011 A1 | 10/2015 |

OTHER PUBLICATIONS

International Search Report and Written Opinion for PCT/US2016/030058 dated Jul. 29, 2016.
Aboitiz et al. "Fiber composition of the human corpus callosum" (Dec. 11, 1992) *Brain Res.* 598(1-2):143-153 (Abstract only).
Albertini et al. "The effect of glycosaminoglycans and proteoglycans on lipid peroxidation" (Aug. 2000) *Int. J. Mol. Med.* 6(2):129-136 (Abstract only).
Alexis et al. "In Vivo Particle Uptake by Airway Macrophages in Healthy Volunteers" (2006) *Am. J. Respir. Cell Mol. Biol.* 34(3):305-313.
Band et al. "Antiproliferative effect of gossypol and its optical isomers on human reproductive cancer cell lines" (Mar. 1989) *Gynecologic Oncology* 32(3):273-277 (Abstract only).
Bandtlow et al. "Proteoglycans in the developing brain: new conceptual insights for old proteins" (Oct. 2000) *Physiol. Rev.* 80(4):1267-1290.
Baran et al. "Important roles for macrophage colony-stimulating factor, CC chemokine ligand 2, and mononuclear phagocytes in the pathogenesis of pulmonary fibrosis" (2007) *Am. J. Respir. Crit. Care Med.* 176(1):78-89.
Bellail et al. "Microregional extracellular matrix heterogeneity in brain modulates glioma cell invasion" (Jun. 2004) *Int. J. Biochem. Cell Biol.* 36(6):1046-1069 (Abstract only).
Beningo et al. "Nascent Focal Adhesions Are Responsible for the Generation of Strong Propulsive Forces in Migrating Fibroblasts" (May 14, 2001) *J. Cell Biol.* 153(4):881-887.
Benz et al. "Biochemical Correlates of the Antitumor and Antimitochondrial Properties of Gossypol Enantiomers" (Jun. 1990) *Mol. Pharma.* 37(6):840-847 (Abstract only).
Benz et al. "Lactic Dehydrogenase Isozymes, $^{31}$P Magnetic-Resonance Spectroscopy, and In Vitro Antimitochondrial Tumor Toxicity With Gossypol and Rhoclamine-123" (Feb. 1987) *J. Clin. Invest.* 79(2):517-523.
Benz et al. "Selective toxicity of gossypol against epithelial tumors and its detection by magnetic resonance spectroscopy" (Mar. 1988) *Contraception* 37(3):221-228 (Abstract only).
Bernstein et al. "Glioblastoma cells do not intravasate into blood vessels" (Jan. 1995) *Neurosurgery* 36(1):124-132 (Abstract only).
Bershadsky et al. "Adhesion-mediated mechanosensitivity: a time to experiment, and a time to theorize" (Oct. 2006) *Curr. Opn. Cell Biol.* 18(5):472-481 (Abstract only).
Binder et al. "Proteases and the Biology of Glioma Invasion" (2002) *J. Neuro-Oncology* 56:149-158.
Bucala et al. "Circulating Fibrocytes Define a New Leukocyte Subpopulation That Mediates Tissue Repair" (Nov. 1994) *Mol. Med.* 1(1):71-81 (Abstract only).
Camoretti-Mercado "Targeting the airway smooth muscle for asthma treatment" (Oct. 2009) *Translational Research* 154(4):165-174 (Abstract only).
Cattaruzza et al. "Proteoglycan control of cell movement during wound healing and cancer spreading" (Sep. 2005) *Matrix Biol.* 24(6):400-417 (Abstract only).

Central Brain Tumor Registry of the United States, Primary Brain Tumors in the United States—Statistical Report 1998-2002, *CBTRUS* 2005-2006.
Chalmers et al. "Chapter 9. Preparative applications of magnetic separation in biology and medicine" (2007) *Laboratory Techniques in Biochemistry and Molecular Biology* 32:249-264 (Abstract only).
Chen et al., Preparation and Characterization of Coaxial Electrospun Thermoplastic Polyurethane/Collagen Compound Nanofibers for Tissue Engineering Applications, *Colloids and Surfaces B-Biointerfaces* (2010), 79(2):315-325.
Chew et al. "The Role of Electrospinning in the Emerging Field of Nanomedicine" 2006, *Curr. Pharm. Sec.* 12(36)A:4751-4770.
Chicoine et al. "Assessment of brain-tumor cell motility in vivo and in vitro" (Apr. 1995) *J. Neurosurg.* 82(4):615-622 (Abstract only).
Choi et al. "Structuring electrospun polycaprolactone nanofiber tissue scaffolds by femtosecond laser ablation" (Nov. 2007) *J. Laser Appl.* 19(4):225-231.
Cukierman et al. "Taking cell-matrix adhesions to the third dimension" (Nov. 23, 2001) *Science* 294:1708-1712.
Dahl et al., "Readily Available Tissue-Engineered Vascular Grafts" (2011) *Science Translational Medicine*, 3(68).
Davies et al. "Adult axon regeneration in adult CNS white matter" (Dec. 1, 1998) *Trends Neurosci.* 21(12):515.
Delpech et al. "Hyaluronan and hyaluronectin in the nervous system" (Sep. 28, 2007) Ciba Foundation Symposium 143—The Biology of Hyaluronan (Abstract only).
Diaz et al. "Controlled encapsulation of hydrophobic liquids in hydrophilic polymer nanofibers by co-electrospinning" (2006) *Adv. Funct. Mater.* 16(16):2110-2116.
Discher et al. "Tissue cells feel and respond to the stiffness of their substrate" (Nov. 18, 2005) *Science* 310:1139-1143.
Drilling et al. "Fabrication of burst pressure competent vascular grafts via electrospinning: Effects of microstructure" (Mar. 15, 2009) *J. Miomed. Mat. Res. Part A* 88A(4):923-934 (Abstract only).
Duling et al. "Mechanical characterization of electrospun Polycaprolactone (PCL): a potential scaffold for tissue engineering" (Feb. 2008) *J. Biomech. Eng.* 130(1) No. 011006 (Abstract only).
Engler et al. "Matrix Elasticity Directs Stem Cell Lineage Specification" (Aug. 25, 2006) *Cell* 126(4):677-689.
Epperly et al. "Correlation of Ionizing Irradiation-induced Late Pulmonary Fibrosis with Long-term Bone Marrow Culture Fibroblast Progenitor Cell Biology in Mice Homozygous Deletion Recombinant Negative for Endothelial Cell Adhesion Molecules" (2004) *In Vivo* 18(1):1-14.
Farin et al. "Transplanted glioma cells migrate and proliferate on host brain vasculature: a dynamic analysis" (Jun. 2006) *Glia* 53(8):799-808 (Abstract only).
Fathallah-Shaykh "Darts in the Dark Cure Animal, but Not Human, Brain Tumors" (May 2002) *Arch. Neurol.* 59:721-724 (Abstract only).
Fujihara et al "Guided bone regeneration membrane made of Polycaprolactone/calcium carbonate composite nano-fibers" (Jul. 2005) *Biomaterials* 26(19):4139-4147 (Abstract only).
Furnari et al. "Malignant astrocytic glioma: genetics, biology, and paths to treatment" (2007) *Genes Dev.* 21:2683-2710.
Gaumer et al. "Structure-function relationships and Source-to-ground Distance and the Mechanical Properties of Electrospun Fiber" *Acta Biomaterialia* 5(5):1552-1561 (Abstract only).
Geiser et al. "The Role of Macrophages in the Clearance of Inhaled Ultrafine Titanium Dioxide Particles" (2008) *Am. J. Respir. Cell Mol. Biol.* 38(3):371-376.
Georges et al. "Cell type-specific response to growth on soft materials" (Apr. 2005) *J. Appl. Physiol.* 98:1547-1553.
Georges et al. "Matrices with compliance comparable to that of brain tissue select neuronal over glial growth in mixed cortical cultures" (Apr. 2006) *Biophys. J.* 90:3012-3018.
Giese et al. "Dichotomy of astrocytoma migration and proliferation" (1996) *Int. J. Cancer* 67:275-282.
Giese et al. "Glioma cell adhesion and migration on human brain sections" (1998) *Anticancer Res.* 18(4A):2435-2447 (Abstract only).
Giese et al. "Migration of Human Glioma Cells on Myelin" (Apr. 1996) *Neurosurgery* 38(4):755-764 (Abstract only).

(56) References Cited

OTHER PUBLICATIONS

Giese et al. "Substrates for astrocytoma invasion" (Aug. 1995) *Neurosurgery* 37(2):294-302 (Abstract only).
Gilbert et al. "Antiproliferative activity of gossypol and gossypolone on human breast cancer cells" (May 26, 1995) *Life Sciences* 57(1):61-67 (Abstract only).
Gladson "The Extracellular Matrix of Gliomas: Modulation of Cell Function" (Oct. 1999) *J. Neuropath. Exper. Neur.* 58(10):1029-1040 (Abstract only).
Goldbrunner et al. "Cell-extracellular matrix interaction in glioma invasion" (1999) *Acta Neurochir (Wien)* 141:295-305.
Grandpre et al. "Nogo: a molecular determinant of axonal growth and regeneration" (Oct. 2001) *Neuroscientist* 7(5):377-386 (Abstract only).
Haley et al. "Study of myelin purity in relation to axonal contamination" (1980) *Cell Mol. Neurobiol.* 1:175-187.
Hashi et al. "Antithrombogenic Property of Bone Marrow Mesenchymal Stem Cells in Nanofibrous Vascular Grafts" Jul. 17, 2007, *PNAS* 104(29) pp. 11915-11920.
He et al. "Fabrication of Drug-Loaded Electrospun Aligned Fibrous Threads for Suture Applications" 2009, J. Biomed. Mater. Research, Part A 89(1):80-95.
Hinz et al. "Alpha-smooth muscle actin expression upregulates fibroblast contractile activity" (Sep. 2001) *Molecular Biology of the Cell* 12(9):2730-2741.
Holland "Glioblastoma multiforme; the terminator" (Jun. 6, 2000) *PNAS USA* 97(12):6242-6244.
Hsu et al. "N,N-Dimethylformamide Additions to the Solution for the Electrospinning of Poly($\epsilon$-caprolactone) Nanofibers" (Apr. 2004) *Macromolecular Materials and Engineering* 289(4):334-340.
Hsu et al. "Nano-sized beads and porous fiber constructs of Poly($\epsilon$-caprolactone) produced by electrospinning" (2004) *Journal of Material Science* 39(9):3003-3013.
Hu et al. "Gossypol inhibits basal and estrogen-stimulated DNA synthesis in human breast carcinoma cells" (1993) *Life Sciences* 53(25):PL433-PL438 (Abstract only).
Hu et al. "Regulating axon growth within the postnatal central nervous system" (Dec. 2004) *Semin Perinatol* 28(6):371-378.
Hu et al. "The proteoglycan brevican binds to fibronectin after proteolytic cleavage and promotes glioma cell motility" (Sep. 5, 2008) *Journal of Biological Chemistry* 283(36):24848-24859.
Huang et al. "A review on polymer nanofibers by electrospinning and their applications in nanocomposites" (Nov. 2003) *Composites Science and Technology* 63(15):2223-2253 (Abstract only).
International Search Report and Written Opinion for PCT/US2015/016973 dated May 22, 2015.
Jaroszewski et al. "Action of Gossypol and Rhodamine 123 on Wild Type and Multidrug-resistant MCF-7 Human Breast Cancer Cells: $^{31}$P Nuclear Magnetic Resonance and Toxicity Studies" (1990) *Cancer Research* 50(21):6936-6943.
Johnson "First-in-the-World Equine Joint Injection for Osteoarthritis" (Jul./Aug. 2014) *The International Equine Veterinarian* 23-25.
Johnson et al. "Electrospun PCL in Vitro: a Microstructural Basis for Mechanical Property Changes" (2009) *Journal of Biomaterials Science, Polymer Edition* 20(4):467-481 (Abstract only).
Johnson et al. "Microstructure-Property Relationships in a Tissue-Engineering Scaffold" (2007) *Journal of Applied Polymer Science* 104(5):2919-2927.
Johnson et al. "Quantitative Analysis of Complex Glioma Cell Migration on Electrospun Polycaprolcatone Using Time-Lapse Microscopy" (2009) *Tissue Engineering Part C* 15(4):531-540.
Jung et al. "Tracking the invasiveness of human astrocytoma cells by using green fluorescent protein in an organotypical brain slice model" (Jan. 2001) *J. Neurosurgery* 94(1):80-89 (Abstract only).
Kang et al. Plasma Treatment of Textiles—synthetic Polymer-Base Textiles (2004) AATCC Review 4(11):29-33.
Katta et al. "Continuous electrospinning of aligned polymer nanofibers onto a wire drum collector" (Sep. 28, 2004) *Nano Letters* 4(11):2215-2218 (Abstract only).

Kazemnejad et al. "Biochemical and Molecular Characterization of Hepatocyte-Like Cells Derived from Human Bone Marrow Mesenchymal Stem Cells on a Novel Three-Dimensional Biocompatible Nanofibrous Scaffold" Feb. 1, 2009, *J. Gastronenter. Hepatol.* 24(2):278-287.
Khil et al. "Novel fabricated matrix via electrospinning for tissue engineering" (2005) *Journal of Biomedical Materials Research Part B—Applied Biomaterials* 72B(1):117-124.
Kim et al. "Controlled protein release from electrospun biodegradable fiber mesh composed of poly($\epsilon$-caprolactone) and poly(ethylene oxide)" (Jun. 29, 2007) *International Journal of Pharmaceutics* 338 (1-2):276-283 (Abstract only).
Kim et al. "Epithelial cell $\alpha 3\beta 1$ integrin links $\beta$-catenin and Smad signaling to promote myofibroblast formation and pulmonary fibrosis" (Jan. 2009) *Journal of Clinical Investigation* 119(1):213-224.
Kleihues et al. "The WHO Classification of Tumors of the Nervous System" (Mar. 2002) *J. Neuropathol. Exp. Neural.* 61(3):215-225 (Abstract only).
Klim et al. "A Defined Glycosaminoglycan-Binding Substratum for Human Pluripotent Stem Cells" (2010) *Nature Methods* 7(23):989-996 (Abstract only).
Ko et al. "High Percentage of False-Positive Results of Cytokeratin 19 RT-PCR in Blood: A Model for the Analysis of Illegitimate Gene Expression" (2000) *Oncology* 59:81-88 (Abstract only).
Kwon et al. "Electrospun nano- to microfiber fabrics made of biodegradable copolyesters: structural characteristics, mechanical properties and cell adhesion potential" (Jun. 2005) *Biomaterials* 26(18):3929-3939.
Lannutti et al. "Electrospinning for tissue engineering scaffolds" (Apr. 2007) *Materials Science and Engineering: C* 27(3):504-509.
Leblanc et al. "An in vitro study of inhibitory activity of gossypol, a cottonseed extract, in human carcinoma cell lines" (Dec. 2002) *Pharmacological Research* 46(6):551-555.
Lee et al. "Characterization of nano-structured poly($\epsilon$-caprolactone) nonwoven mats via electrospinning" (Feb. 2003) *Polymer* 44(4):1287-1294.
Lesma et al. "Glycosaminoglycans in nerve injury: I. Low doses glycosaminoglycans promote neurite formation" (Dec. 1, 1996) *J. Neurosci. Res.* 46(5):565-571.
Levicar et al. "Proteases in brain tumour progression" (2003) *Acta Neurochir. (Wien.)* 145:825-838.
Levina et al. "Chemotherapeutic drugs and human tumor cells cytokine network" (2008) *International Journal of Cancer* 123(9):2031-2040.
Li et al. "A three-dimensional nanofibrous scaffold for cartilage tissue engineering using human mesenchymal stem cells" (Feb. 2005) *Biomaterials* 26(6):599-609.
Li et al. "Biological response of chondrocytes cultured in three-dimensional nanofibrous poly($\epsilon$-caprolactone) scaffolds" (Dec. 15, 2003) *Journal of Biomedical Materials Research Part A* 67A(4):1105-1114.
Li et al. "Electrospinning nanofibers as uniaxially aligned arrays and layer-by-layer stacked films" (Feb. 2004) *Advanced Materials* 16(4):361-366.
Li et al. "Multilineage differentiation of human mesenchymal stem cells in a three-dimensional nanofibrous scaffold" (Sep. 2005) *Biomaterials* 26(25):5158-5166.
Liang et al. "Developing gossypol derivatives with enhanced antitumor activity" (1995) *Investigational New Drugs* 13(3):181-186.
Lieblein et al. "STAT3 can be activated through paracrine signaling in breast epithelial cells" (2008) *BMC Cancer* 8(302):1-14 :302.
Liu et al. "Function analysis of estrogenically regulated protein tyrosine phosphatase $\gamma$ (PTP$\gamma$) in human breast cancer cell line MCF-7" (2004) *Oncogene* 23(6):1256-1262.
Liu et al. "Involvement of breast epithelial-stromal interactions in the regulation of protein tyrosine phosphatase-$\gamma$ (PTP$\gamma$) mRNA expression by estrogenically active agents" (2002) *Breast Cancer Research and Treatment* 71(1):21-35.
Liu et al. The (−)-enantiomer of gossypol possesses higher anticancer potency than racemic gossypol in human breast cancer: (2002) *Anticancer Research* 22(1A):33-38.

(56) References Cited

OTHER PUBLICATIONS

Liu et al. "Transformation of MCF-10A Human Breast Epithelial Cells by Zeranol and Estradiol-17beta" (Nov.-Dec. 2004) *Breast J.* 10(6):514-521 (Abstract only).
Lo et al. "Cell movement is guided by the rigidity of the substrate" (Jul. 2000) *Biophysical Journal* 79(1);144-152.
Luu et al. "Development of a nanostructured DNA delivery scaffold via electrospinning of PLGA and PLGA and PLA-PEG block copolymers" (Apr. 29, 2003) *Journal of Controlled Release* 89(2):341-353.
Macchiarini et al. "Clinical Transplantation of a Tissue-Engineered Airway" (Dec. 13, 2008) *The Lancet* 372(9655):2023-2030.
Martins et al. "Electrospun nanostructured scaffolds for tissue engineering applications" (2007) *Nanomedical* 2(6):929-942.
Mathews, "Preparation and anisotropic mechanical behavior of highly-oriented electrospun poly(butylene terephthalate) fibers" (Aug. 2006) *Journal of Applied Polymer Science* 101(3):2017-2021.
McClure et al. "A Three-Layered Electrospun Matrix to Mimic Native Arterial Architecture Using Polycaprolactone, Elastin, and Collagen: A Preliminary Study" 2010, *Acta Biomaterialia* 6:2422-2433.
Morawski et al. "Perineuronal nets potentially protect against oxidative stress" (Aug. 2004) *Exp. Neurol.* 188(2):309-315.
Morgenstern et al. "Chondroitin sulphate proteoglycans in the CNS injury response" (2002) *Prog. Brain Res.* 137:313-332.
Mori et al. "Fibrocytes contribute to the myofibroblast population in wounded skin and originate from the bone marrow" (Mar. 10, 2005) *Experimental Cell Research* 304(1):81-90.
Murray et al. "Hyper-responsiveness of IPF/UTP fibroblasts: Interplay between TGF β1, IL-13 and CCL2" (2008) 40(10):2174-2182.
Nam et al. "Improved Cellular Infiltration in Electrospun Fiber via Engineered Porosity" (Sep. 2007) *Tissue Engineering* 13(9):2249-2257.
Nam et al. "Materials selection and residual solvent retention in biodegradable electrospun fibers" (Feb. 5, 2008) *Journal of Applied Polymer Science* 107(3):1547-1524.
Nam et al. "Novel Electrospun Scaffolds for the Molecular Analysis of Chondrocytes Under Dynamic Compression" 2009, *Tissue Engineering Part A* 15(3):513-523.
Ninomiya et al. "Transforming Growth Factor-β Signaling Enhances Transdifferentiation of Macrophages into Smooth Muscle-Like Cells" (2006) *Hypertension Research* 29(4):269-276.
Norton et al. "Myelination in rat brain: method of myelin isolation" (Oct. 1973) *J. Neurochem.* 21(4):749-757.
Novak et al. "Extracellular matrix and the brain: components and function" (2000) *J. Clin. Neurosci.* 7(4):280-290.
Ohnishi et al. "A Novel Model of Glioma Cell Invasion Using Organotypic Brain Slice Culture" (Jul. 15, 1998) *Cancer Res.* 58:2935-2940.
Palfi et al. "Correlation of in vitro infiltration with glioma histological type in organotypic brain slices" (2004) *Br. J. Cancer* 91(4):745-752.
Pelham Jr. et al. "Cell locomotion and focal adhesions are regulated by substrate flexibility" (Dec. 1997) *PNAS USA* 94:13661-13665.
Pham et al., Electrospinning of Polymeric Nanofibers for Tissue Engineering Applications: A Review, Tissue Engineering (2006), 12(5):1197-1211.
Pilkington "The paradox of neoplastic glial cell invasion of the brain and apparent metastatic failure" (1997) *Anticancer Res.* 17(6B):4103-4105 (Abstract).
Powell et al. "EDC cross-linking improves skin substitute strength and stability" (2006) *Biomaterials* 27(34): 5821-5827.
Properzi et al. "Proteoglycans and Brain Repair" (Feb. 2004) *News Physiol. Sci.* 19:33-38.
Quigley et al. "The relationship between survival and the extent of the resection in patients with supratentorial malignant gliomas" (1991) *Neurosurgery* 29:385-389.
Rao "Molecular mechanisms of glioma invasiveness: the role of proteases" (Jul. 2003) *Nature Reviews Cancer* 3:489-501.
Rath et al. "Compressive Forces Induce Osteogenic Gene Expression in Calvarial Osteoblasts" (2008) *Journal of Biomechanics* 41(5):1095-1103.
Rauch "Extracellular matrix components associated with remodeling processes in brain" (2004) *Cell Mol. Life Sci.* 61:203102045.
Reneker et al. "Nanometre diameter fibres of polymer, produced by electrospinning" (1996) *Nanotechnology* 7(3):216-223.
Rocks et al. "ADAMTS-1 Metalloproteinase Promotes Tumor Development through the Induction of a Stromal Reaction In vivo" (2008) *Cancer Research* 68(22):9541-9550.
Ruoslahti "Brain extracellular matrix" (1996) *Glycobiologhy* 6(5):489-492.
Sasmono et al. "A macrophage colony-stimulating factor receptor—green fluorescent protein transgene is expressed throughout the mononuclear phagocyte system of the mouse" (2003) *Blood* 101(3):1155-1163.
Saunders et al. "Fibrocyte localization to the airway smooth muscle is a feature of asthma" (Feb. 2009) *Journal of Allergy and Clinical Immunology* 123(2): 376-384.
Schiffer et al. "Cell proliferation and invasion in malignant gliomas" (1997) *Anticancer Research* 17(1A):61-69 (Abstract only).
Schmidt et al. "Identification of Circulating Fibrocytes as Precursors of Bronchial Myofibroblasts in Asthma" (2003) *Journal of Immunology* 171(1):380-389.
Shin et al. "Contractile cardiac grafts using a novel nanofibrous mesh" (Aug. 2004) *Biomaterials* 25(17):3717-3723.
Shin et al. "In Vivo Bone Tissue Engineering Using Mesenchymal Stem Cells on a Novel Electrospun Nanofibrous Scaffold" (Jul. 9, 2004) *Tissue Engineering* 10(1-2):33-41.
Sieben et al. "PCR artifacts in LOH and MSI analysis of microdissected tumor cells" (Nov. 2000) *Human Pathology* 31(11):1414-1419.
Silver et al. "Regeneration beyond the glial scar" (Feb. 2004) *Nature* 5:146-156.
Srikar et al. "Desorption-limited mechanism of release from polymer nanofibers" (2008) *Langmuir* 24(3):965-974.
Stein et al. "Estimating the cell density and invasive radius of three-dimensional glioblastoma tumor spheroids grown in vitro" (Aug. 1, 2007) *Applied Optics* 46(22):5110-5118.
Stitzel et al. "Controlled Fabrication of a Biological Vascular Substitute" 2006, *Biomaterials* 27:1088-1094.
Subramanian et al. "Metastasis to and from the central nervous system—the 'relatively protected site'" (Aug. 2002) *The Lancet Oncology* 3(8):498-507.
Swanson et al. "A quantitative model for differential motility of gliomas in grey and white matter" (Oct. 2000) *Cell Proliferation* 33(5):317-329.
Swanson "Quantifying glioma cell growth and invasion in vitro" (2008) *Mathematical and Computer Modeling* 47:638-648.
Teo et al. "A review on electrospinning design and nanofibre assemblies" (2006) *Nanotechnology* 17(14):R89-R106.
Teo et al. "Electrospun fibre bundle made of aligned nanofibers over two fixed points" (1978) *Nanotechnology* 16:1878-1884.
Thomas et al. "Effects of gossypol on the cell cycle phases in T-47D human breast cancer cells" (Jul.-Aug. 1991) *Anticancer Research* 11(4):1469-1476 (Abstract only).
Tomlinson et al. "Loss of heterozygosity analysis: Practically and conceptually flawed?" (2002) *Genes Chromosomes & Cancer* 34:349-353.
Tonn et al. "Mechanisms of glioma cell invasion" (2003) *Acta Neurochir* Suppl 88: 163-167.
Toole "Hyaluronan and its binding proteins, the hyaladherins" (1990) *Curr. Opin. Cell Biol.* 2:839-844.
Tse, et al. "Current Status of Pipeline Embolization Device in the Treatment of Intracranial Aneurysms: A review" (Dec. 2013) *World Neurosurgery* 80(6): 829-835.
Tuszynski et al. "Differential cytotoxic effect of gossypol on human melanoma, colon carcinoma, and other tissue culture cell lines" (Feb. 1984) *Cancer Research* 44(2):768-771.
Van Meter et al. "The role of matrix metalloproteinase genes in glioma invasion: co-dependent and interactive proteolysis" (2001) *Journal of Neuro-Oncology* 53:213-235.

(56) References Cited

OTHER PUBLICATIONS

Viapiano et al. "BEHAB/brevican requires ADAMTS-mediated proteolytic cleavage to promote glioma invasion" (2008) *J. Neurooncol.* 88:261-272.
Viapiano et al. "From barriers to bridges: chondroitin sulfate proteoglycans in neuropathology" (Oct. 2006) *Trends Mol. Med.* 12(10):488-496.
Vuorinen et al. "Debulking or biopsy of malignant glioma in elderly people—a 9andomized study" (2003) *Acta Neurochir.* 145:5-10.
Wang et al. "Conjugated Linoleic Acid (CLA) Up-regulates the Estrogen-regulated Cancer Suppressor Gene, Protein Tyrosine Phosphatase γ (PTPγ), in Human Breast Cells" (2006) *Anticancer Research* 26(1A):27-34.
Wang et al. "Effect of gossypol on DNA synthesis and cell cycle progression of mammalian cells in vitro" (Jan. 1984) *Cancer Research* 44(1):35-38.
Wang et al. "Nanofibres and their Influence on Cells for Tissue Regeneration" (2005) *Aust. J. Chem.* 58(10):704-712.
Wang et al. "Increased Circulating Fibrocytes in Asthma with Chronic Airflow Obstruction" (2008) *Am. J. Respir. Crit. Care Med.* 178(6): p. 583-591.
Williams et al. "Anti-glioma effects of protein kinase inhibitors that simultaneously block invasion and proliferation" (Oct. 2007) Abstracts from 12$^{th}$ Annual Meeting of the Society for Neuro-Oncology 9: 486 ET-18 (Abstract only).
Wu et al. "Versican protects cells from oxidative stress-induced apoptosis" (Feb. 2005) *Matrix Biology* 24(1):3-13.
Wu et al. "An in vitro and in vivo study of antitumor effects of gossypol on human SW-13 adrenocortical carcinoma" (1986) *Cancer Research* 49(14):3754-3758.
Wykosky et al. "Soluble monomeric EphrinA1 is released from tumor cells and is a functional ligand for the EphA2 receptor" (2008) *Oncogene* 27(58):7260-7273.
Xie et al. "Encapsulation of protein drugs in biodegradable microparticles by co-axial electrospray" Jan. 15, 2008) *Journal of Colloid and Interface Science* 317(2):469-476.
Xie et al. "White matter inhibitors in CNS axon regeneration failure" (Feb. 2007) *Exp. Neurol.* 209(2):302-312.
Yamaguchi "Lecticans: organizers of the brain extracellular matrix" (2000) *Cell Mol. Life Sci.* 57:276-289.
Yang et al. "Integrin α1β1 and α2β1 are the key regulators of hepatocarcinoma cell invasion across the fibrotic matrix microenvironment" (Dec. 1, 2003) *Cancer Research* 63(23): 8312-8317.
Yoo et al. "Surface-Functionalized Electrospun Nanofibers for Tissue Engineering and Drug Delivery" Jan. 1, 2009, *Advanced Drug Delivery Reviews* 61:1033-1042.
Yoshimoto et al. "A biodegradable nanofiber scaffold by electrospinning and its potential for bone tissue engineering" (May 2003) *Biomaterials* 24(12):2077-2082.
Yu et al. "Production of submicrometer diameter fibers by two-fluid electrospinning" (Sep. 2004) *Adv. Mater.* 16(17):1562-1566.
Zborowski et al. "Red blood cell magnetophoresis" (Apr. 2003) *Biophysical Journal* 84:2638-2645.
Zeng et al. "Enzymatic degradation of poly(L-lactide) and poly(ε-caprolactone) electrospun fibers" (Dec. 15, 2004) *Macromolecular Bioscience* 4(12):1118-1125.
Zeng et al. "Ultrafine fibers electrospun from biodegradable polymers" (Jul. 25, 2003) *Journal of Applied Polymer Science* 89(4):1085-1092.
Zhang et al. "Electrospinning of gelatin fibers and gelatin/PCL composite fibrous scaffolds" (2005) *J. Biomed. Mater. Res. Part B: Appl. Biomater.* 72B(1):156-165.
Zhang et al. "Recent development of polymer nanofibers for biomedical and biotechnological applications" (2005) *Journal of Materials Science—Materials in Medicine* 16(10):933-946.
Meng et al., Electrospun aligned nanofibers composite of MWCNT/polyurethane to enhance vascular endothelium cells proliferation and function, *Journal of Nanoscience and Nanotechnology* (Jul. 8, 2010) pp. 312-320.
International Search Report and Written Opinion for International Application No. PCT/US2016/060157 dated Jan. 31, 2017.
Lee et al., "Biomedical Applications of Magnetically Functionalized Organic/Inorganic Hybrid Nanofibers," International Journal of Molecular Sciences (Jun. 15, 2015), 16 pp. 13661-13677.
Samios et al., "In situ compatibilization of polyurethane with poly(ethylene terephthalate)," Department of Chemistry, European Polymer Journal (2000), 36 pp. 937-947.
Ayres et al., "Microvascular Endothelial Cell Migration in Scaffolds of Electrospun Collagen," Wound Repair and Regeneration (Mar. 2005), 13(2):A6 (abstract only).
Park, Lab-made organ implanted for first time, (Jul. 14, 2017), CNN.com, <http://www.cnn.com/2011/HEALTH/07/07/trachea.transplant/index.html>.
Supplemental European Search Report and Written Opinion for EP15774154 dated Sep. 22, 2017.

* cited by examiner

NANOFIBER SCAFFOLDS FOR BIOLOGICAL STRUCTURES

CROSS-REFERENCE TO RELATED APPLICATIONS

This patent application claims the benefit of U.S. Provisional Patent Application Ser. No. 61/585,869 filed on Jan. 12, 2012, and entitled "Biocompatible Nanofiber Materials for Biological Structures," the disclosure of which is hereby incorporated by reference herein in its entirety and made part of the present U.S. utility patent application for all purposes.

BACKGROUND OF THE INVENTION

Tissue engineering involves the synthesis of biologically relevant tissue for a wide range of applications including wound healing and the replacement or support of damaged organs. A common strategy is culturing target specific cells in vitro in a scaffold followed by implantation of the scaffold in a biological organism. As a logical cellular source for tissue engineering, stem cells have attracted a great deal of attention due to their relatively fast proliferation rate and diverse differentiation potential to various phenotypes. These include cells derived from several origins: induced pluripotent stem cells from fibroblasts, mesenchymal stem cells from bone marrow and adult stem cells from adipose tissue. Stem cells distinctively self-renew and their terminal differentiation depends on the influence of soluble molecules (e.g., growth factors, cytokines) as well as physical and biochemical interactions with scaffolds. Cellular behavior and subsequent tissue development at the cell-scaffold interface therefore involve adhesion, motility, proliferation, differentiation and functional maturity. The physicochemical properties of a scaffold, such as bulk chemistry, surface chemistry, topography, three-dimensionality and mechanical properties, all influence cellular response. Bulk chemistry can control cytotoxicity, as most scaffolds are made of biodegradable materials and must eventually release the by-products of their degradation. The effect of surface chemistry is often mediated by instantly adsorbed proteins such as fibronectin, collagen, fibrinogen, vitronectin, and immunoglobulin that affect phenotype, viability, and morphology, as well as proliferation and differentiation.

Studies regarding the effect of surface topography and texture on cellular response have been conducted. Stem cells are known to recognize topographical features of the order of hundreds of nanometers to several micrometers, and exhibit distinctive genomic profiles in the absence of biochemical differentiation cues and a commitment to terminal differentiation. Electrospun scaffolds are ideal matrices for two dimensional or three dimensional culture of the cells providing non-woven nano- to micro-sized fibrous microstructures typically having relative porosities of 70-90%. Natural biodegradable materials such as collagen, gelatin, elastin, chitosan, and hyaluronic acid, as well as synthetic biodegradable polymers such as poly(e-caprolactone) (PCL), poly(glycolic) acid (PGA) and poly(lactic) acid (PLA), have been electrospun for chondral and osseous applications.

In general, the broad utility of electrospun scaffolds for tissue engineering, wound healing, and organ replacement is clear (see *Modulation of Embryonic Mesenchymal Progenitor Cell Differentiation via Control Over Pure Mechanical Modulus in Electrospun Nanofibers*, Nama et al., Acta Biomaterialia 7, 1516-1524 (2011), which is incorporated by reference herein in its entirety, for all purposes) and the present invention provides polymer fiber constructs for these and other applications. Alignment of fibers produced during electrospinning has previously been achieved by various methods including, for example, high velocity collection of fibers (e.g., on the surface of a high velocity rotating mandrel) and alternating collection of fibers from one grounded electrode to another on an immobile surface or in the air. Current methods of electrospinning aligned fibers are not known to achieve the ideal alignment of fibers observed in the human body, such as, for example, in brain tissue. Therefore, improvements in alignment must be made in order to obtain the high degree of alignment necessary for an in vitro model of human tissue.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a synthetic construct suitable for transplantation into a biological organism is provided. This construct includes a synthetic construct suitable for transplantation into a biological organism, comprising: a two-dimensional or three-dimensional polymer scaffold, wherein the shape and dimensions of the polymer scaffold are based on a native biological structure, wherein the polymer scaffold further includes at least one layer of polymer fibers that have been deposited by electrospining, and wherein the orientation of the fibers in the scaffold relative to one another is substantially parallel; and wherein, optionally, the polymer scaffold has been preseeded with at least one type of biological cell prior to implantation into a biological organism, and wherein the at least one type of biological cell is operative to facilitate integration of the polymer scaffold into the organism so that the polymer scaffold may function in a manner significantly similar to or the same as the native structure.

In accordance with another aspect of the present invention, a system for manufacturing an artificial construct suitable for transplantation into a biological organism is provided. This system includes: a two or three three-dimensional preform that is based on the actual two or three-dimensional structure of a native mammalian tissue; and an electrospinning apparatus, wherein the electrospinning apparatus is operative to deposit at least one layer of polymer fibers on the preform to form a polymer scaffold, and wherein the orientation of the fibers in the scaffold relative to one another is substantially aligned or parallel.

In yet another aspect of this invention, a system for manufacturing an artificial construct suitable for transplantation into a biological organism for wound healing purposes is provided. This system includes a two or three three-dimensional preform that is based on the actual two or three-dimensional structure of a native mammalian tissue; an electrospinning apparatus, wherein the electrospinning apparatus is operative to deposit at least one layer of polymer fibers on the preform to form a polymer scaffold, and wherein the orientation of the fibers in the scaffold relative to one another is substantially parallel; and a least one type of biological cell for preseeding onto the polymer scaffold, and wherein the at least one type of biological cell further includes autologous cells or allogeneic cells, and wherein the autologous cells or allogeneic cells further include cord blood cells, embryonic stem cells, induced pluripotent cells, mesenchymal cells, placental cells, bone marrow derived cells, hematopoietic cell, epithelial cells, endothelial cells, fibroblasts and chondrocytes.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein.

DETAILED DESCRIPTION OF THE INVENTION

Figure 1:
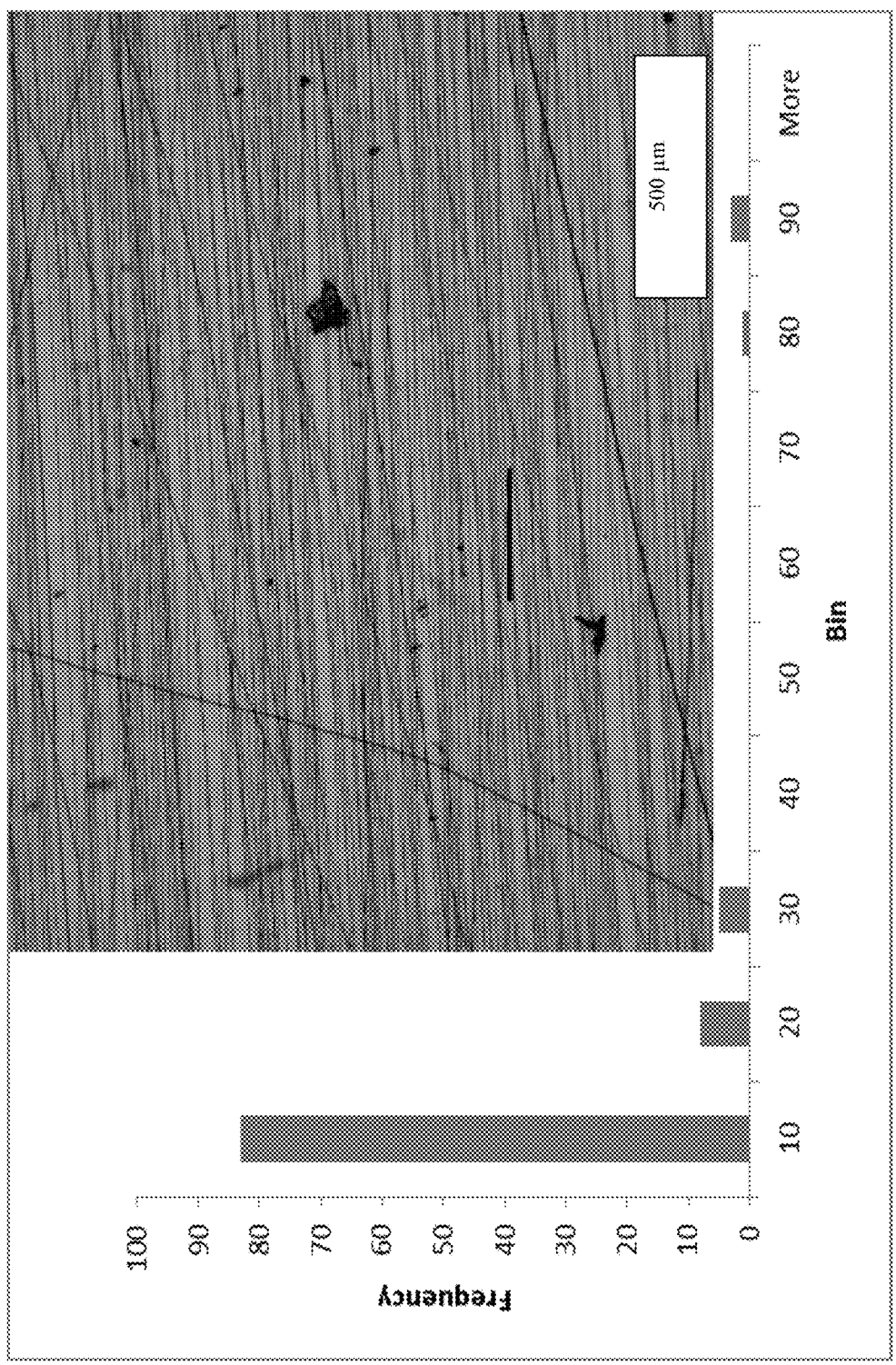
FIG. 1 depicts electrospun PCL fibers spun without an anti-static bar for 10 minutes at 0.5 ml/h, +4 kV on the needle, and −4 kV on the mandrel and the plot shows the angle of the fibers from horizontal.

Exemplary embodiments of the present invention are now described with reference to the Figures. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

With reference to the Figures, this invention relates generally to the construction of implantable artificial tissues for humans and/or animals, and more specifically to a process or method for manufacturing two-dimensional polymer microscale and nanoscale structures for use as scaffolds in the growth of biological structures. The use of these scaffolds in creating or repairing numerous and multiple biological tissues and structures, is contemplated by and included in this invention. Exemplary versions of the manufacturing process of this invention include preparing a preform or substrate that is based on an actual native tissue and/or organ; electrospinning one or more layers of nanoscale (less than 1000 nanometers) or microscale (less than 50 microns) polymer fibers on the preform to form a nanofiber-based scaffold. The fibers are typically formed by electrospinning by extruding a polymer solution from a fiberization tip; creating an electronic field proximate to the fiberization tip; and positioning a ground or opposite polarity within the preform. The preform may be rotated to align the fibers on the preform or a second ground or polarity may be placed in the preform and rapidly switching the electric field to align the fibers. The microscale and nanoscale polymer fibers may be randomly aligned or maybe substantially parallel or both. These nanofiber structures may be seeded with one or more types of biological cells prior to implantation in the body to increase the rate of tissue growth into the scaffold. The polymer scaffold may include autologous or allogeneic cells such as cord blood cells, embryonic stem cells, induced pluripotent cells, mesenchymal cells, placental cells, bone marrow derived cells, hematopoietic cell, epithelial cells, endothelial cells, fibroblasts, chondrocytes or combinations thereof. These biological cells may be applied to the surface of the scaffold or distributed throughout the scaffold matrix utilizing perfusion within a bioreactor. The polymer fibers may also be coated or otherwise treated with at least one compound that is operative to promote cellular attachment to the scaffold or promote engraftment of the scaffold into the biological organism. The at least one compound may be selected from the group consisting of proteins, peptides, cytokines, growth factors, antibiotic compounds, anti-inflammatory compounds, and combinations thereof.

Choosing a material that accurately mimics the mechanical properties of the native tissue or organ may promote proper stem cell differentiation and facilitate normal function of the replacement tissue or organ. Included materials may be non-resorbable for permanent implantation or may be designed to slowly degrade while the host body rebuilds the native tissue. In the latter case, the implanted prosthesis will eventually be completely resorbed. Permanent (i.e., non-resorbable) polymers may include polyurethane, polycarbonate, polyester terephthalate and degradable materials may include polycaprolactone, polylactic acid, polyglycolic acid, gelatin, collagen, or fibronectin. The fibers may be electrospun onto a preform with the desired prosthesis shape. An exemplary mandrel (preform) may be coated with Teflon or similar material to facilitate removal of the scaffold after deposition or a slight taper (e.g., about 1°) can be manufactured into the mandrel. Nearly any size or shape can be produced from the electrospun fibers by using a pre-shaped form and the fiber deposition methods of the present invention.

Closely mimicking the structural aspects of the tissue or organ is important with regard to replicating the function of the native tissue or organ. By controlling the orientation of the fibers and assembling a composite structure of different materials and/or different fiber orientations it is possible to control and direct cell orientation and differentiation. Fiber orientation can be altered in each layer of a composite or sandwich scaffold in addition to the material and porosity to most closely mimic the native tissue. A properly constructed scaffold will permit substantially complete cellular penetration and uniform seeding for proper function and prevention of necrotic areas developing. If the fiber packing is too dense, then cells may not be able to penetrate or migrate from the exposed surfaces into the inner portions of the scaffold. However, if the fiber packing is not close enough, then attached cells may not be able to properly fill the voids, communicate and signal each other and a complete tissue or organ may not be developed. Controlling fiber diameter can be used to change scaffold porosity as the porosity scales with fiber diameter. Alternatively, blends of different polymers may be electrospun together and one polymer preferentially dissolved to increase scaffold porosity. The properties of the fibers can be controlled to optimize the fiber diameter, the fiber spacing or porosity, the morphology of each fiber such as the porosity of the fibers or the aspect ratio, varying the shape from round to ribbon-like. The precursor solution described below may be controlled to optimize the modulus or other mechanical properties of each fiber, the fiber composition, and/or the degradation rate (from rapidly biosoluable to biopersitent). The fibers may also be formed as drug eluting fibers, anti-bacterial fibers or the fibers may be conductive fibers, radio opaque fibers to aid in positioning or locating the fibers in an x-ray, CT or other scan.

In accordance with this invention, the process of electrospinning is driven by the application of a high voltage, typically between 0 and 30 kV, to a droplet of a polymer solution or melt at a flow rate between 0 and 50 ml/h to create a condition of charge separation between two electrodes and within the polymer solution to produce a polymer jet. A typical polymer solution would consist of a polymer such as polycaprolactone, polystyrene, or polyethersulfone and a solvent such as 1,1,1,3,3,3-Hexafluoro-2-propanol, N,N-Dimethylformamide, acetone, or tetrahydrofuran in a concentration range of 1-50 wt %. As the jet of polymer solution travels toward the electrode it is elongated into small diameter fibers typically in the range of 0.1-100 μm.

In preparing an exemplary scaffold, a polymer nanofiber precursor solution is prepared by dissolving 2-30 wt % polyethylene terephthalate (PET) (Indorama Ventures) in a mixture of 1,1,1,3,3,3-hexafluoroisopropanol (HFIP) and trifluoroacetic acid and the solution is heated to 60° C. followed by continuous stirring to dissolve the PET. The solution may be cooled to room temperature and the solution placed in a syringe (e.g., 60 cc) with a blunt tip needle (e.g., 20 gauge). The nanofibers are formed by electrospinning using a high voltage DC power supply (Glassman High Voltage, Inc., High Bridge, N.J.) set to 1 kV-40 kV (e.g., +15 kV) positive or negative polarity, a 5-30 cm (e.g., 15 cm) tip-to-substrate distance, and a 1 μl/hr to 100 mL/hr (e.g., 10 ml/hr) flow rate. It is possible to use a needle array including a large number of needles (e.g., >1000) to increase system output. Fiber diameter may be controlled by the viscosity of the precursor solution and the solvent used and suitable exemplary fibers are in the range of 100 nanometer 30 microns. Approximately 0.2-3 mm (e.g., 1 mm) thickness of randomly oriented and/or highly-aligned fibers may be deposited onto the form, followed by polymer rings added, followed by an additional approximately 0.2-3.0 mm (e.g., 2 mm) of fiber added while the form is rotated. The scaffold may be placed in a vacuum overnight to ensure removal of residual solvent (typically less than 10 ppm) and treated using a radio frequency gas plasma for 1 minute to make the fibers more hydrophilic and promote cell attachment. Samples may be storied in re-closeable polyethylene bags, or the like.

In accordance with this invention, an exemplary preparation of electrospinning solution typically includes polyethylene terephthalate (PET), polycaprolactone (PCL), polylactic acid (PLA), polyglycolic acid (PGA), polyetherketoneketone (PEKK), polyurethane (PU), polycarbonate (PC), polyamide (Nylon), natural polymers such as fibronectin, collagen, gelatin, hyaluronic acid or combinations thereof that are mixed with a solvent and dissolved. Suitable solvents include acetone, dimethylformamide, trifluoroacetic acid, hexafluoroisopropanol, acetic acid, dimethylacetamide, chloroform, dichloromethane, water, ionic compounds, or combinations thereof. A form is prepared for the deposition of nanofibers. Optionally, simulated cartilage or other supportive tissue may be applied to the form and the fibers are then sprayed onto or transferred onto a form to build up the scaffold.

During electrospinning, polymer fibers are driven toward a collector by charge separation caused by applied voltage. The collector typically is a conductive surface, such as, for example, aluminum or copper, and in this disclosure the collector is covered by a thin layer of plastic, ranging, for example, between about 0.001-0.1 inches thick. The charge that drives electrospinning toward the collector is derived from mobile ions within the polymer solution or melt. The jet of polymer that is produced has a net positive or negative charge, depending upon the polarity of the voltage applied to the electrode(s). When the jet solidifies on the collector surface, a charge builds up as subsequent fiber layers are collected. As the charge builds up on the surface, fiber with similar charge is repelled leading to irregularly arranged fibers and thus a lower degree of alignment. To reduce the effects of surface charge, an anti-static device (e.g., bar) may be incorporated into the process to improve fiber alignment. The anti-static bar bombards the surface of a sample with positively and negatively charged ions in the form of, for example, a plasma or corona discharge to neutralize the charge on the substrate. Therefore, as fiber builds up, successive layers of fibers will deposit more uniformly side-by-side (parallel relationship) to increase the alignment. The position of the anti-static bar is generally parallel to the surface of the collection mandrel, wheel, device, plate, etc. and is for example, about 0.5-3 inches away from the surface.

Figure 2:
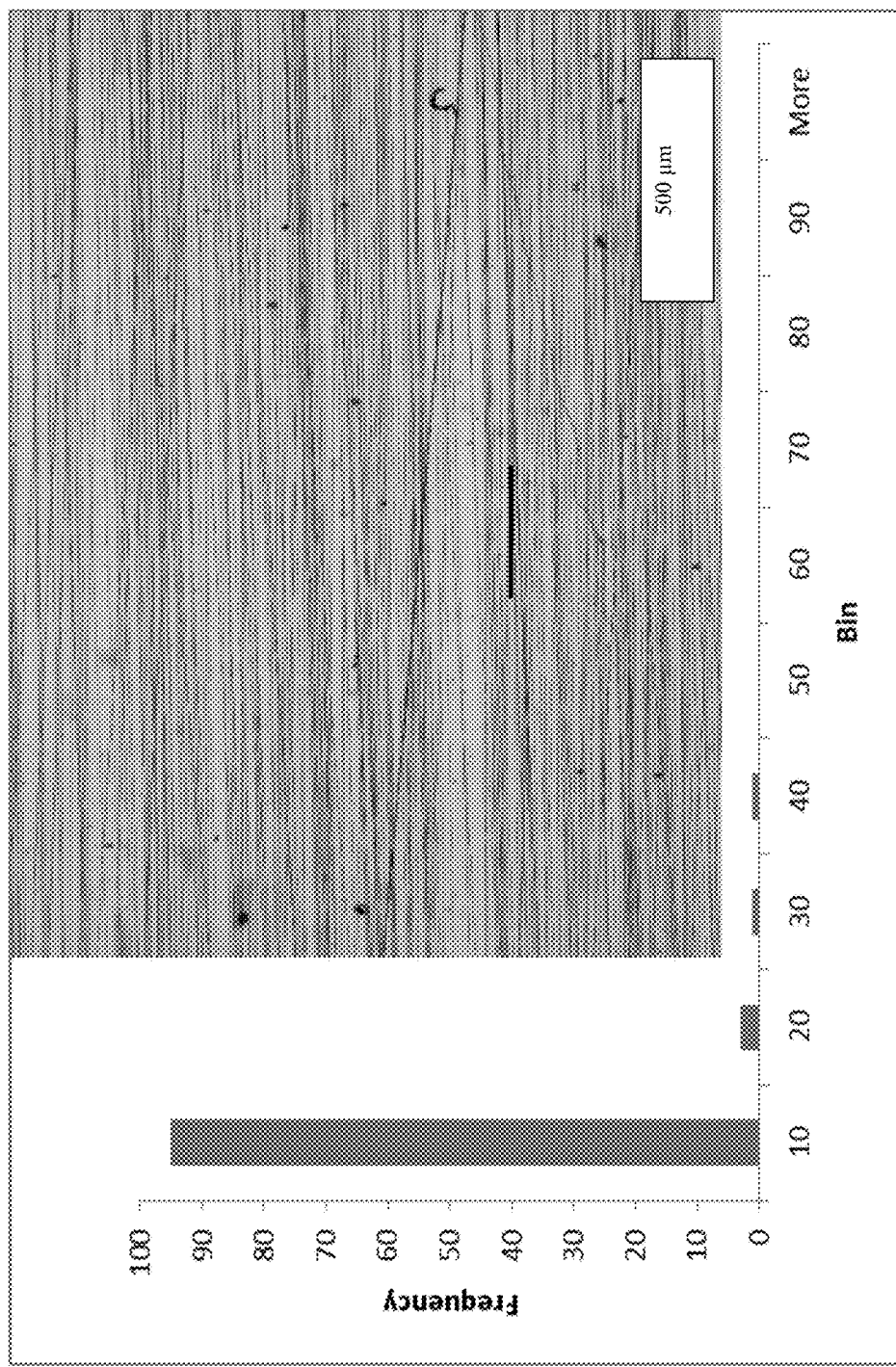
FIG. 2 depicts electrospun PCL fibers spun with an anti-static bar for 10 minutes at 0.5 ml/h, +4 kV on the needle, and −4 kV on the mandrel and the plot shows the angle of the fibers from horizontal.
Figure 3:
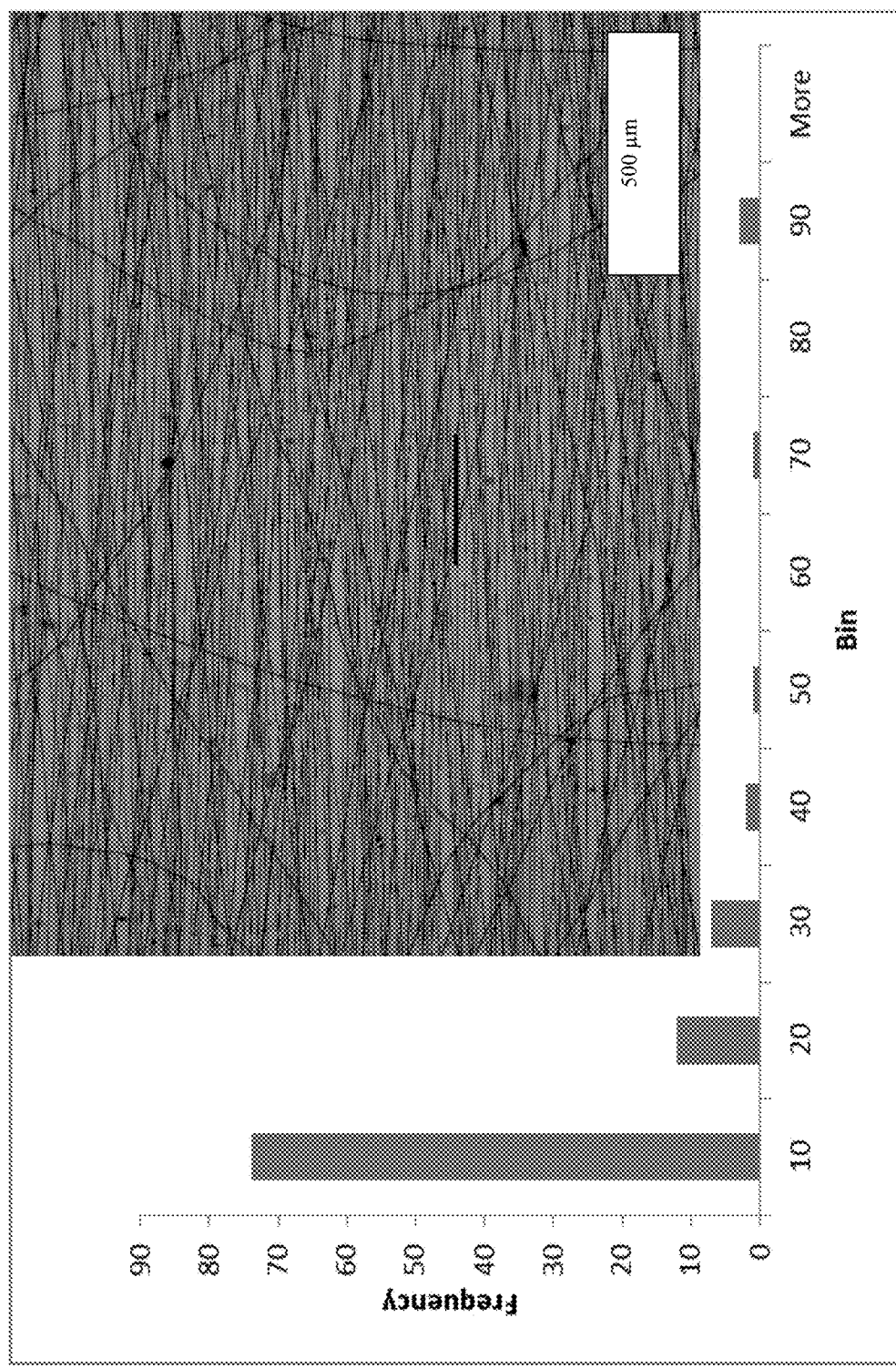
FIG. 3 depicts electrospun PCL fibers spun without an anti-static bar at 1.0 ml/h and the plot shows the angle of the fibers from horizontal.
Figure 4:
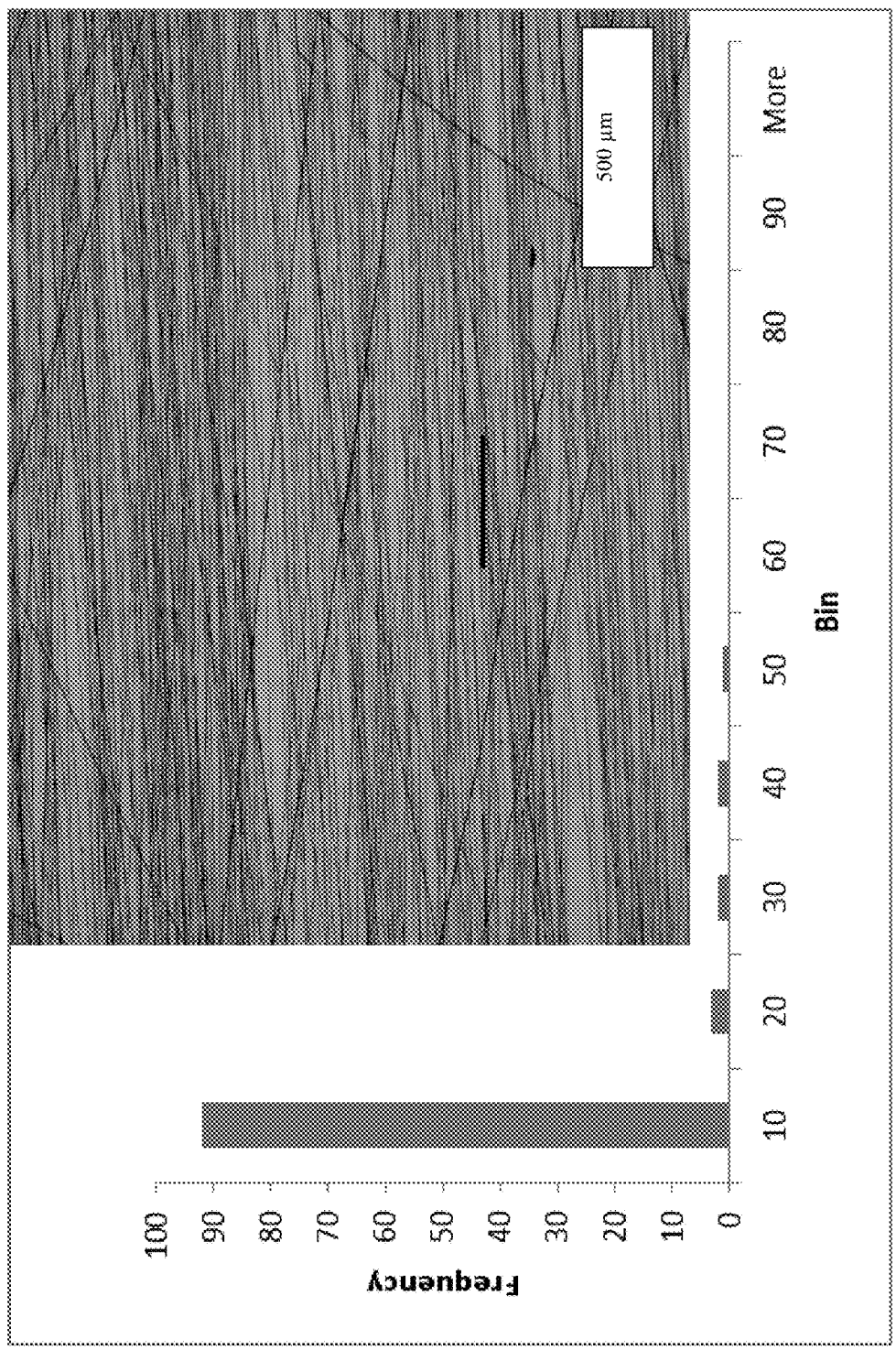
FIG. 4 depicts electrospun PCL fibers spun with an anti-static bar at 1.0 ml/h and the plot shows the angle of the fibers from horizontal.
Figure 5:
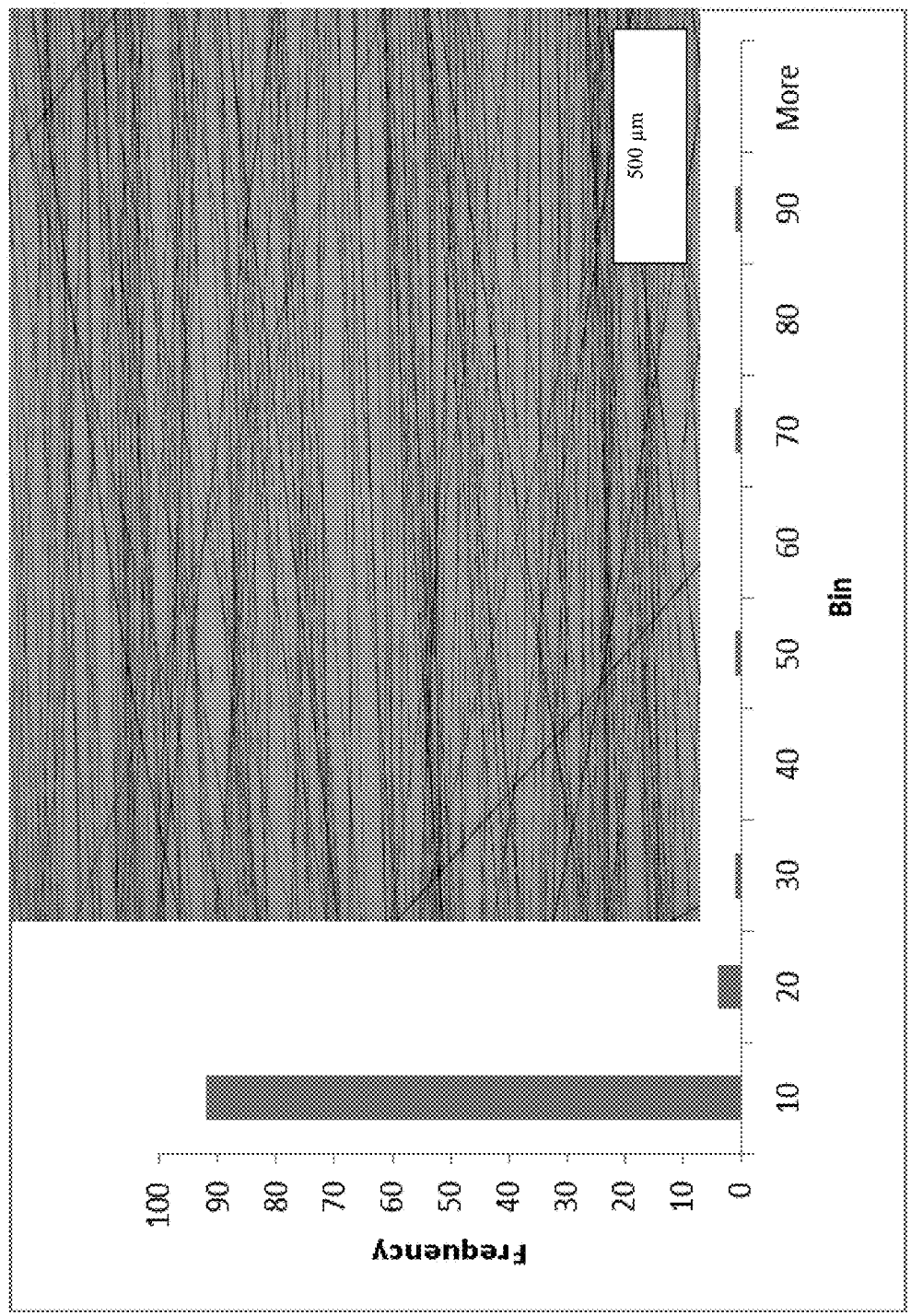
FIG. 5 depicts electrospun PCL fibers spun using a dual syringe setup with two anti-static bars, wherein each needle has a flow rate of 1.0 ml/h and the plot shows the angle of the fibers from horizontal.
Figure 6:
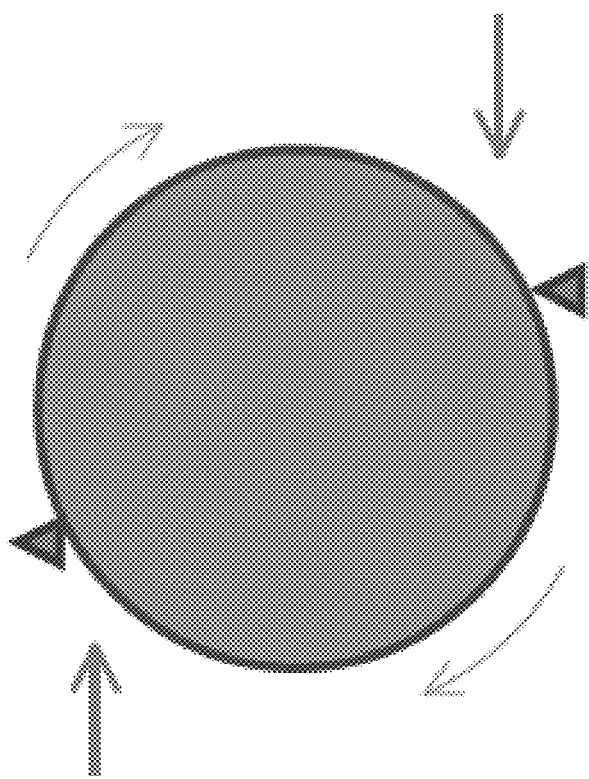
FIG. 6 depicts a dual syringe electrospinning setup, wherein the triangles indicate the relative positions of the first and second anti-static bars, wherein the straight arrows indicate relative locations of the syringe pump with polymer solution, and wherein the clockwise arrows indicate the rotation direction of the fiber collection mandrel at the center of the image.

Experimental results demonstrate that fiber alignment was improved significantly with the addition of an anti-static bar (or a device having similar functional properties), when compared to samples spun under the same conditions without the anti-static bar. FIG. 1 shows the alignment of a sample to be 83%, when electrospun without a static bar; while FIG. 2 shows a 12% increase in fiber alignment to 95%, when a static bar treats the surface during spinning. An additional benefit of anti-static bars is the ability to electrospin using multiple needles. FIG. 3 shows a sample spun at 1 ml/h without a static bar; while FIG. 4 shows a sample spun at 1 ml/h with an anti-static bar, and FIG. 5 shows a sample spun using a dual syringe configuration and two anti-static bars treating a wheel surface where the fibers are being deposited. When fibers are spun without an anti-static bar (see FIG. 3), the fiber alignment is low, with only 74% of fibers collected in a low angle orientation. With an anti-static bar, under the same spinning conditions, the alignment becomes 92% (see FIG. 4). Additionally, alignment is maintained at 92% (see FIG. 5) when multiple needles are used for electrospinning, and when two anti-static bars treat the wheel surface as illustrated in FIG. 6. This demonstrates the ability to scale-up the production rate by incorporating additional needles and anti-static devices. Antistatic bars (or, alternately, one or more ionizing guns) may also be used to create continuous (i.e., very long) fibers that are continuously aligned.

Figure 7:
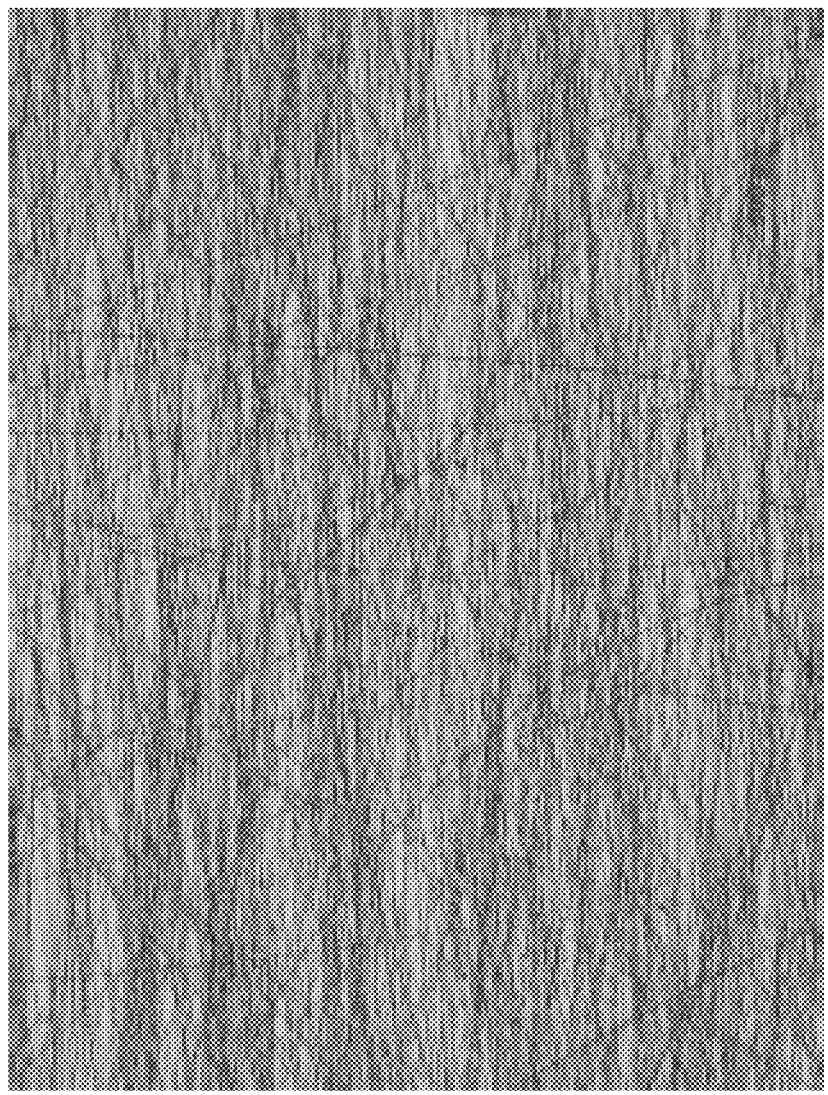
FIG. 7 depicts electrospun PCL fibers spun with an anti-static bar at 1.0 ml/h, wherein an alternating ground was not applied during electrospinning.
Figure 8:
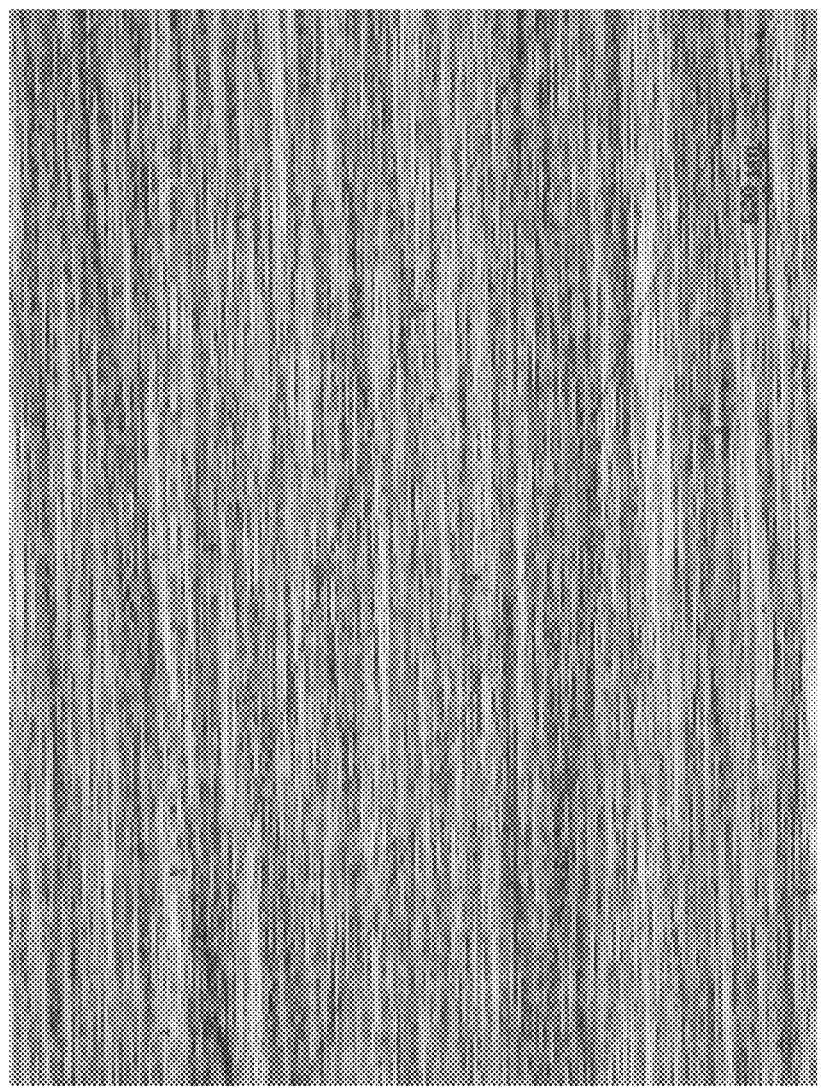
FIG. 8 depicts electrospun PCL fibers spun with an anti-static bar at 1.0 ml/h, wherein an alternating ground was applied during electrospinning.
Figure 9:
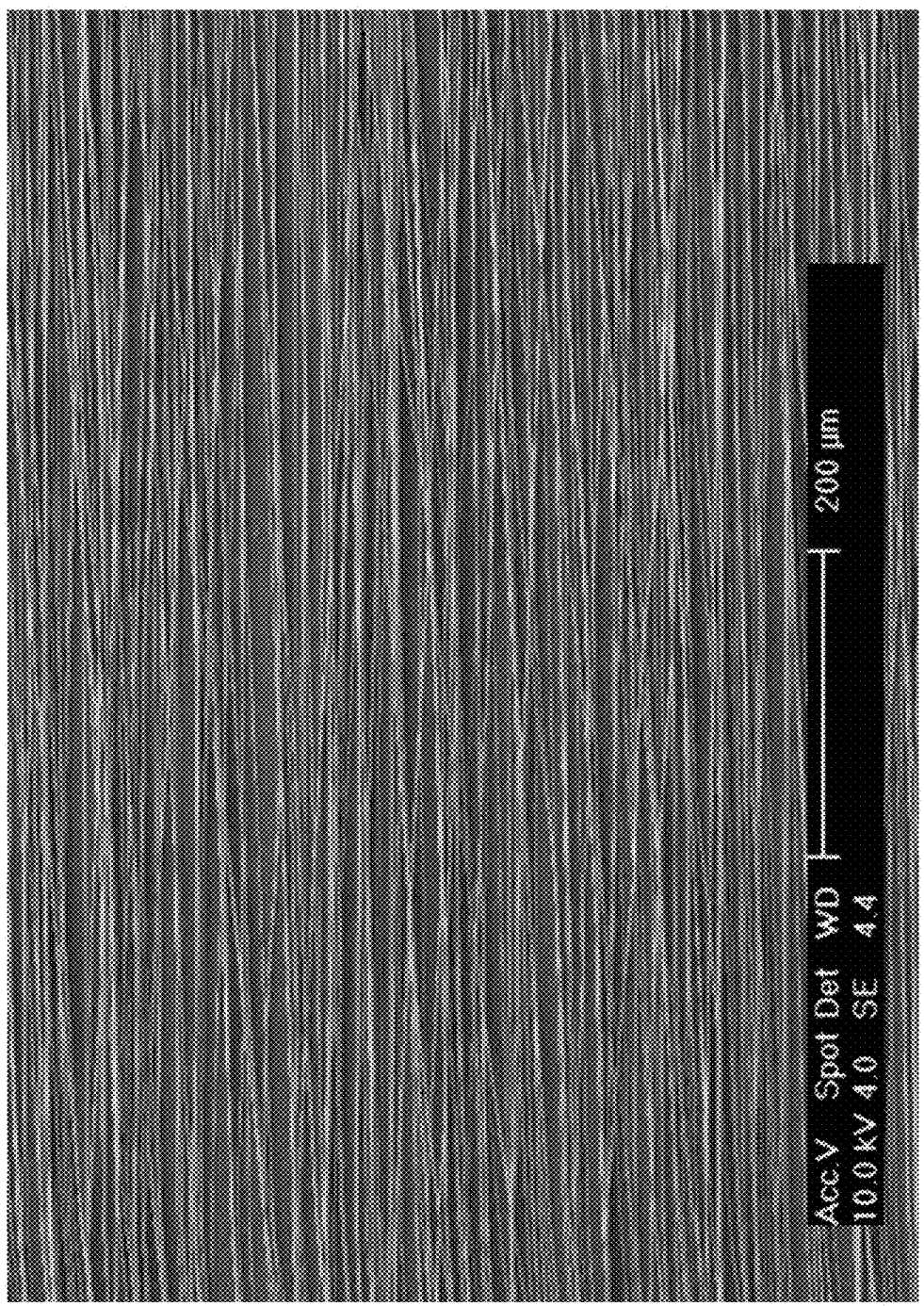
FIG. 9 is a scanning electromicrograph of the polymer nanofibers used in the present invention.
Figure 10:
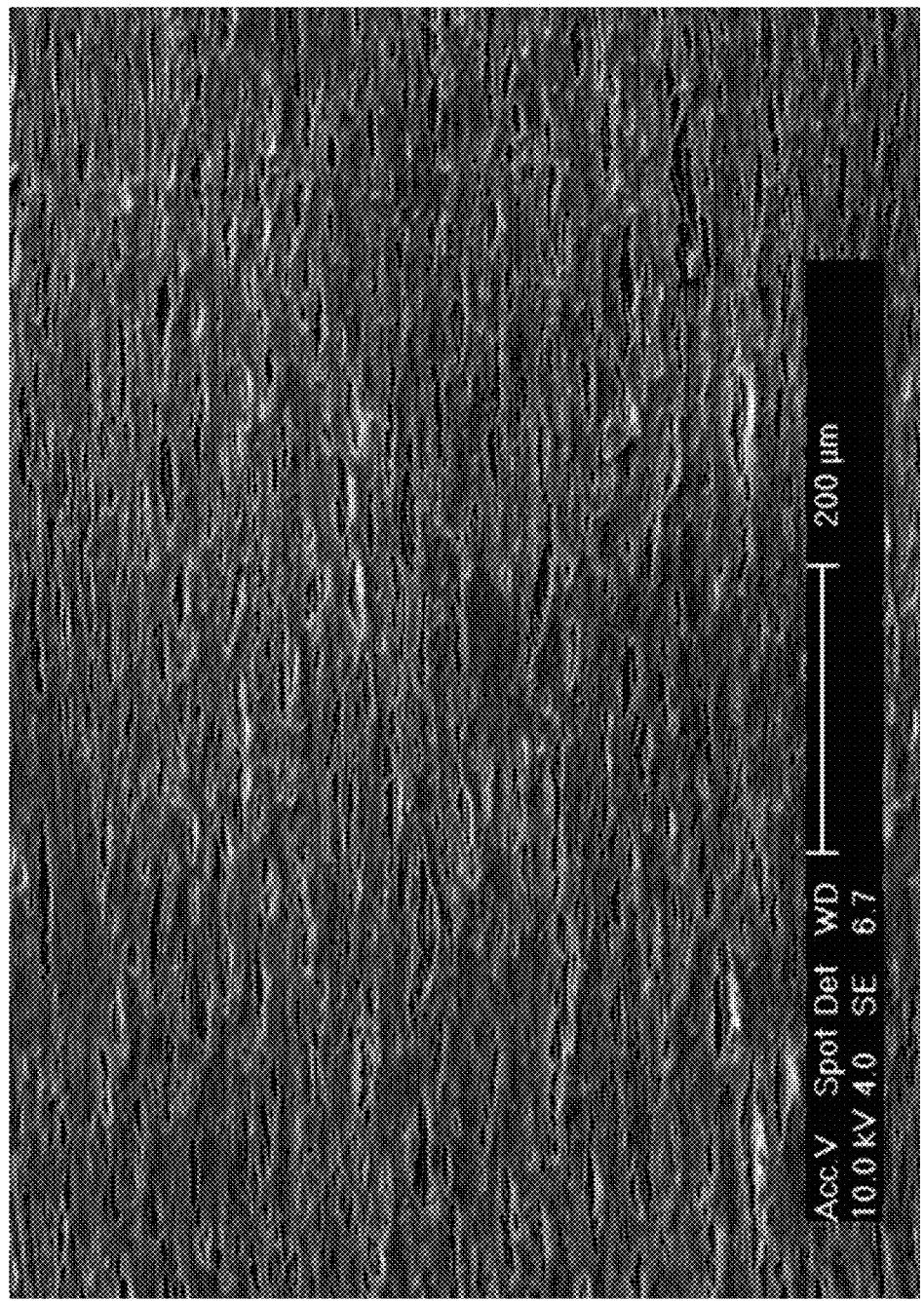
FIGS. 10-11 are scanning electromicrographs of the polymer nanofibers used in the present invention with a coating of marrow stromal cells.
Figure 11:
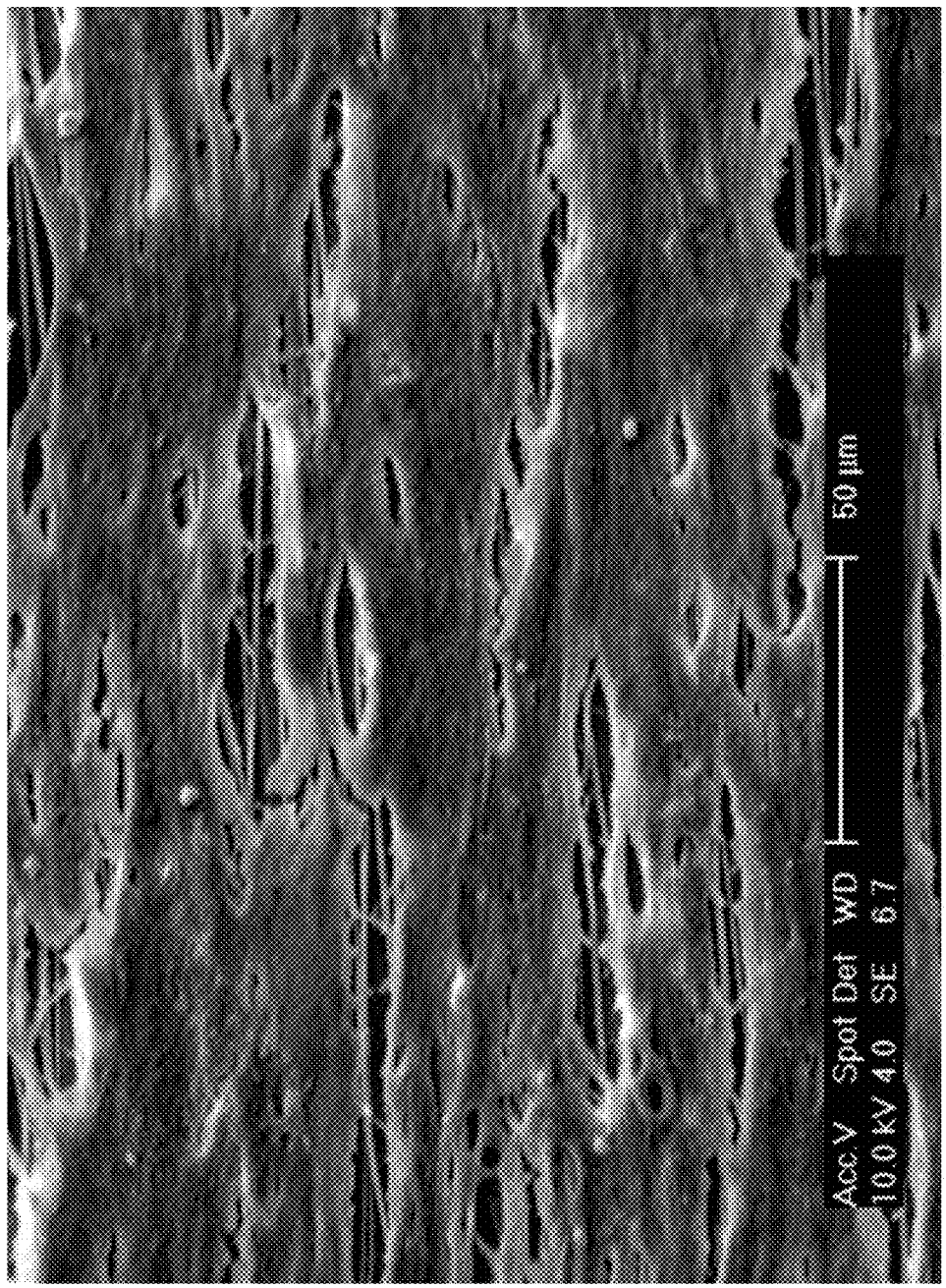
Figure 12:
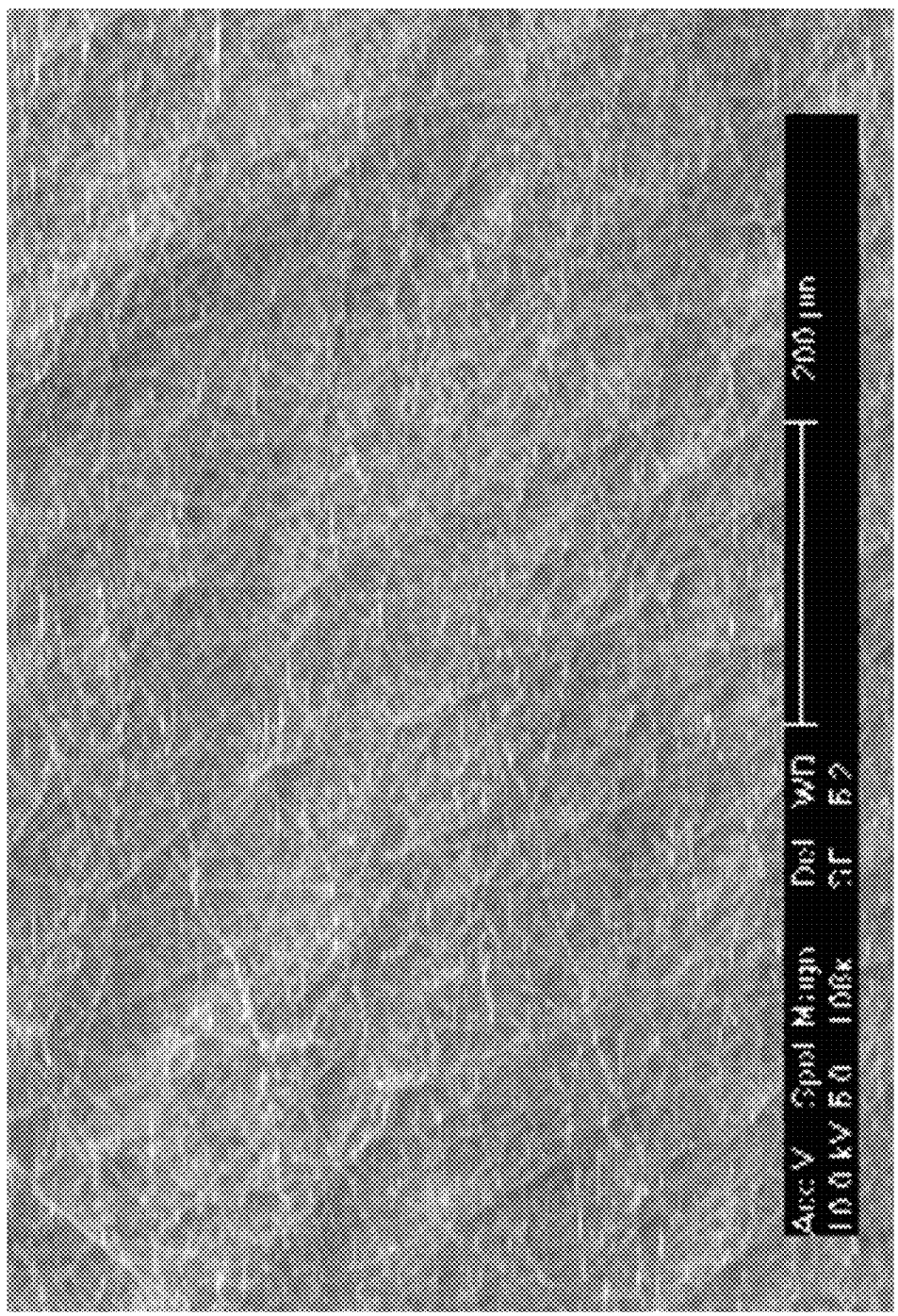
FIG. 12 is a scanning electromicrograph of the polymer nanofibers used in the prior art.
Figure 13:
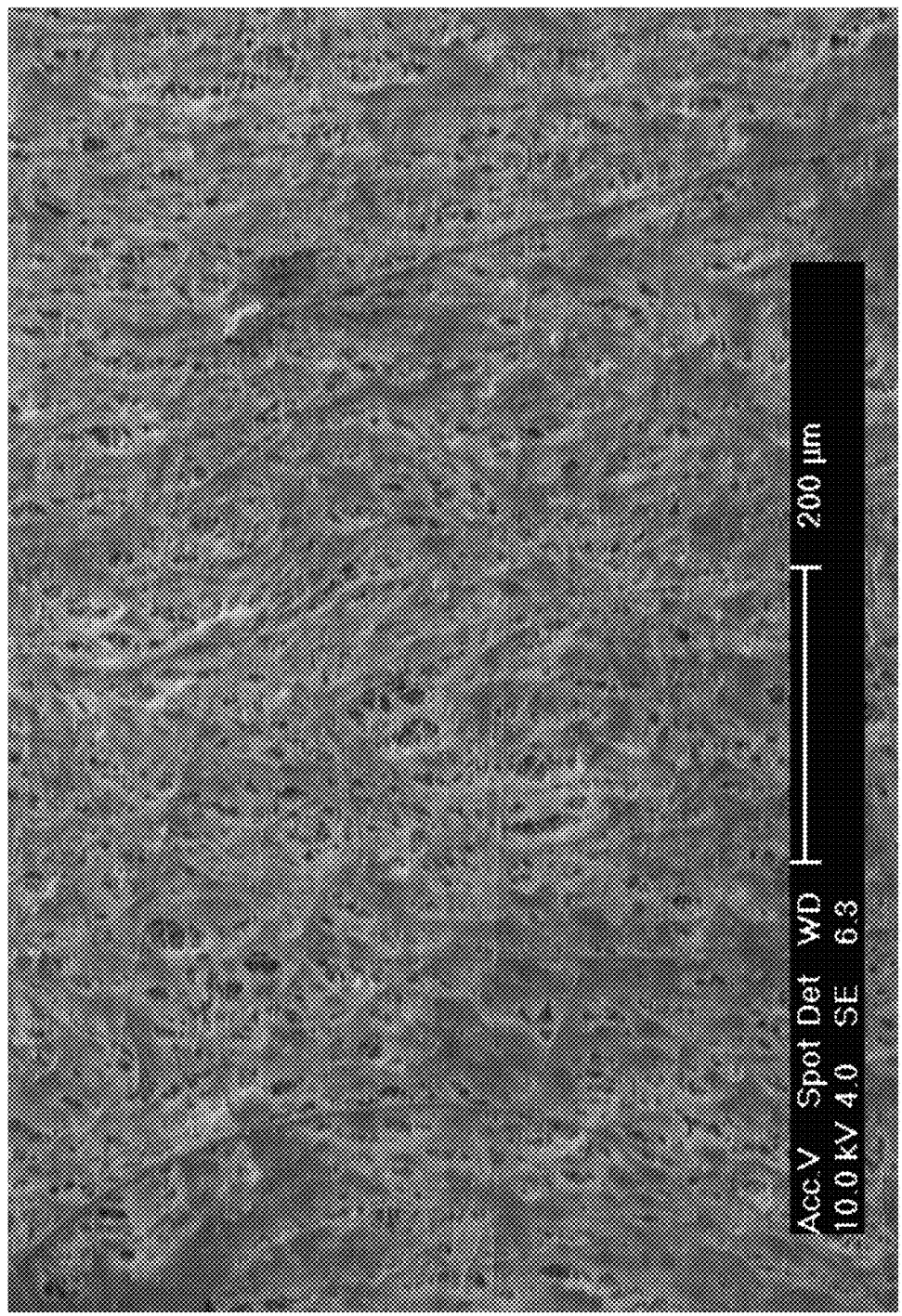
FIG. 13 is a scanning electromicrograph of the polymer nanofibers used in the prior art with a coating of marrow stromal cells.

As previously indicated, the alternating collection of fibers from one ground to the next will create aligned fiber. High velocity collection of fibers, such as on the surface of a rotating mandrel, will achieve similar results. When the two methods are combined, alternating grounds on a rotating mandrel, the fiber alignment is enhanced beyond what either method typically achieves. The combined method of fiber alignment is highly effective when the surface of the mandrel is coated in a thin insulating layer, such as, for example, polystyrene. An alternating ground is established by securing a continuous plastic sheet and wrapping conductive tape around the surface of the wheel, or a similar method that creates alternating layers of conductive and non-conductive surface material. The conductive tape generally is made of, for example, carbon or copper and ranges between about 0.1-2 inches wide and is spaced uniformly around the wheel circumference. This tape should be connected to the charged/grounded wheel for the alternating ground effect to be obtained. FIGS. 7-8 illustrate the alternating ground effect. FIG. 7 shows a sample that was electrospun without the alternating ground and with an anti-static bar. FIG. 8 shows a sample that was electrospun with both the alternating ground and anti-static bar. These images demonstrate the dramatic improvement in alignment when using the alternating ground and anti-static bar on a high-speed mandrel.

With reference to FIGS. 9-13, the polymer fiber scaffolds of the present invention may be used to manufacture two-dimensional biocompatible patches of varying thickness for use in humans or animals (e.g., primates, cats, dogs, horses and cattle) as an aid in wound healing involving muscles, internal organs, bones, cartilage, and/or external tissues. Biocompatible materials, which are suitable for use in medical applications within the body or on external surfaces, typically elicit little or no immune response in human or veterinary applications. In one or more exemplary embodiments, these patches include substantially parallel electrospun nanoscale and microscale polymer fibers. These patches may be seeded with biological cells prior to use to increase the rate of tissue growth into the patch. Such biological cells may include autologous or allogenic cells such as cord blood cells, embryonic stem cells, induced pluripotent cells, mesenchymal cells, placental cells, bone marrow derived cells, hematopoietic cells, epithelial cells, endothelial cells, fibroblasts and chondrocytes. Examples of internal uses include tissue, ocular tissue (lens, cornea, optic nerve or retina), intestinal tissue, internal organs such as the liver, kidney, spleen, pancreas, esophagus, trachea, uterus, stomach, bladder, muscles, tendons, ligaments, nerves, dura matter and other brain structures, dental structures, blood vessels and other bodily structures. Examples of external uses may include wound dressings, burn and abrasion coverings, and recovery aides to inhibit the formation of scar tissue. External structures are typically the skin but may include the cornea or surface of the eye, the ear canal, the mouth and nasal passages or the nail bed.

An exemplary method for making the biocompatible patches of this invention includes depositing a layer of substantially parallel electrospun polymer fibers on a preform (i.e., a wheel or similar structure) to form a fiber patch or gap filling material; and applying donor cells to the patch. Preferably, the fibers are formed byelectrospinning by extruding a polymer solution from a fiberization tip; creating an electronic field proximate to the fiberization tip; and positioning a ground within the deposition surface. The preform may be rotated to align the fibers on the surface or a second ground or opposite polarity may be placed in the preform and rapidly switching the ground. To speed the growth of human tissue into the fiber preform, the fibers are aligned by rapidly spinning the preform so that alignment of the structure produced by standard electrospinning while the fibers are drawn into a substantially parallel ordering by the tension created by spinning the form. See generally, *Preparation and anisotropic mechanical behavior of highly-oriented electrospun poly(butylene terephthalate) fibers*, Journal of Applied Polymer Science Volume 101, Issue 3, pages 2017-2021 (August 2006), which is incorporated by reference herein, in its entirety. A split ground technique, in which fiber deposition rapidly alternates between two separate grounding plates within the preform or by alternating the electric field is also an effective method of forming parallel fibers on the preform. See, generally, *Electrospinning Nanofibers as Uniaxially Aligned Arrays and Layer-by-Layer Stacked Films*, Advanced Materials Volume 16, Issue 4, pages 361-366 (February 2004), which is incorporated by reference herein, in its entirety. Fiber alignment can be further enhanced by controlling certain variables such as humidity, solvents, flow rates, and rotational speeds. Lower relative humidity (e.g., 20%) results in better overall alignment than higher relative humidity (e.g., 50%). However, deposition efficiency is increased in higher humidity (e.g., deposition on plastic). The use of certain solvents such as acetone typically reduce fiber alignment, while others such as 1,1,1,3,3,3-Hexafluoro-2-propanol typically increase alignment. Decreasing the flow rate at which the polymer solution is being pumped typically increases fiber alignment, while increasing the flow rate decreases fiber alignment. Finally, increasing the rotational speed of the wheel upon which the fiber is being deposited typically increases fiber alignment.

The thickness of the patch may be from a few microns for application to surfaces to speed cellular growth and inhibit scarring to several centimeters for use as a plug for insertion into a wound or to speed the growth of structures in a specific direction. High thickness patches are useful in repairing infracted cardiac tissue, esophageal or tracheal tissue or supporting the growth of nerve in a predetermined direction. Depending on the material used in preparing the fibers the patch may dissolve within the body after a predetermined time or may be relatively permanent for longer term applications. It is also possible to fabricate a multipart structure which includes one or more layers of dissolvable fibers with one or more layers of more permanent fibers.

Having generally described this aspect of the present invention, further understanding can be obtained by reference to certain specific examples detailed below, which are provided for purposes of illustration only and are not intended to be all inclusive or limiting unless otherwise specified.

EXAMPLE 1

In Example 1, patch material was formed by fiber spinning the precursor solution at a deposition rate of 1 ml/h at a tip to substrate distance of 20 cm, while rotating the surface at a rate of 478 RPM (15.7 m/s) for a period of 2 hours, using a +/−4.2 kV field. The resulting fibers had an alignment of about 91% (that is, 91% of the fibers had a fiber angle within 10° from the spinning direction of the wheel).

EXAMPLE 2

In Example 2, patch material was formed by fiber spinning the precursor solution at a deposition rate of 1 ml/h at a tip to substrate distance of 20 cm, while rotating the surface at a rate of 478 RPM (15.7 m/s) for a period of 2 hours, using a +/−5.0 kV field. The resulting fibers had an alignment of about 75%.

EXAMPLE 3

In Example 3, patch material was formed by fiber spinning the precursor solution at a deposition rate of 1 ml/h at a tip to substrate distance of 20 cm, while rotating the surface at a rate of 478 RPM (15.7 m/s) for a period of 2 hours, using a +/−4.8 kV field. The resulting fibers had an alignment of about 98%.

In this embodiment, to speed the growth of human tissue into the fiber preform, the fibers were aligned by rapidly spinning the preform so that alignment of the structure produced by standard electrospinning while the fibers were drawn into a substantially parallel ordering by the tension created by spinning the form. The properties of the fibers can be controlled to optimize the fiber diameter, the fiber spacing or porosity, the morphology of each fiber such as the porosity of the fibers or the aspect ratio, varying the shape from round to ribbon-like. The precursor solution may be controlled to optimize the modulus or other mechanical properties of each fiber, the fiber composition, the degradation rate (from rapidly biosoluable to biopersitent. The fibers may also be formed as drug eluting fibers, anti-bacterial fibers or the fibers may be conductive fibers, radio opaque fibers to aid in positioning or locating the fibers in an x-ray, CT or other scan.

Typically the fibers used in the patches are formed by electrospinning; however, fibers may also be formed by methods such as extrusion and drawing of a fiber, ink jet printing fibers, or mechanically stretching a fiber sheet to attenuate and align the fibers. An exemplary ink jet method includes preparing solutions for ink jet printing as follows: a 1 mg/m solution of fibronectin in DI water wis diluted with additional DI water at a ratio of 1:4; DiI cyanine dye is then added at a ratio of 1:100 to a 1 mg/ml solution of hylauronic acid in DI water. A concentrated solution of purified myelin is diluted at a ratio of 1:9 in PBS then DiI cyanine dye is added at a ratio of 1:100. The solutions are printed onto a substrate using an industrial grade ink jet printer (Jetlab II, Microfab Technologies, Inc. Plano, Tex.) with a glass capillary tip with an orifice diameter of 50 microns. A drop frequency of 180 Hz is used with a head speed of 5 mm/s. A custom made program script may be used to create printed patterns.

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

What is claimed:

1. A synthetic construct consisting of:
   a single layer of electrospun polymer fibers, wherein at least about 75% of the fibers have a fiber angle within about 10° of parallel;
   wherein the single layer has a shape of a patch and a thickness from about 0.2 mm to about 3 mm.

2. The synthetic construct of claim 1, wherein the electrospun polymer fibers comprise a natural polymer selected from the group consisting of collagen, gelatin, fibronectin, hyaluronic acid, and combinations thereof.

3. The synthetic construct of claim 1, wherein about 92% of the electrospun polymer fibers have a fiber angle within about10° of parallel.

4. The synthetic construct of claim 1, wherein the electrospun polymer fibers comprise a polymer selected from the group consisting of polyethylene terephthalate, polycaprolactone, polylactic acid, polyglycolic acid, polyetherketoneketone, polyurethane, polycarbonate, polyamide, and combinations thereof.

5. A system comprising:
   a rotatable preform based on a structure of a native mammalian tissue; and
   an electrospinning apparatus comprising at least one anti-static bar;
   wherein the at least one anti-static bar is positioned from about 0.5 inches to about 3 inches away from the rotatable preform.

6. The system of claim 5, wherein the electrospinning apparatus includes a fiberization tip.

7. A method of making a synthetic construct, the method comprising:
   creating an electronic field of about 1-40 kV proximate to a fiberization tip;
   positioning a first ground within a preform;
   positioning at least one anti-static device from about 0.5 inches to about 3 inches away from the preform;
   rotating the preform in a rotation direction at a rotation rate;
   extruding from the fiberization tip at a flow rate a polymer solution comprising a polymer and a solvent; and
   depositing by electrospinning a plurality of polymer fibers on the preform, wherein at least about 75 % of the electrospun polymer fibers deposited have a fiber angle within about 10° from the rotation direction of the preform.

8. The method of claim 7, wherein the solvent is selected from the group consisting of acetone, dimethylformamide, trifluoroactic acid, hexafluoroisopropanol, acetic acid, dim ethylacetamine, chloroform, dichloromethane, water, ionic compounds, and combinations thereof.

9. The method of claim 7, wherein the at least one anti-static device is an anti-static bar.

10. The method of claim 7, wherein the rotation rate is about 15.7 meters per second.

11. The method of claim 7, wherein the percentage of the electrospun polymer fibers having a fiber angle within about 10 degrees of the rotation direction of the preform is selected from the group consisting of about 75%, about 91%, about 92%, and about 98%.

12. The method of claim 7, wherein the preform further comprises a second ground.

13. The method of claim 12, wherein the depositing by electrospinning further comprises alternating a ground between the first ground and the second ground.

14. The method of claim 7, wherein the flow rate is about 1.0 ml/h.

15. The method of claim 7, wherein the polymer is selected from the group consisting of polyethylene terephthalate, silicone, polyurethane, polycarbonate, polyether ketone, polycaprolactone, polylactic acid, polyglycolic acid, and combinations thereof.

* * * * *